United States Patent
Du et al.

(10) Patent No.: US 9,763,684 B2
(45) Date of Patent: Sep. 19, 2017

(54) DEVICES AND METHODS FOR REMOVING OCCLUSIONS FROM A BODILY CAVITY

(71) Applicant: Med-Sonics Corp., Erie, PA (US)

(72) Inventors: Shu Du, Erie, PA (US); Tao Song, Erie, PA (US)

(73) Assignee: Med-Sonics Corporation, Erie, PA (US)

( * ) Notice: Subject to any disclaimer, the term of this patent is extended or adjusted under 35 U.S.C. 154(b) by 189 days.

(21) Appl. No.: 14/677,330

(22) Filed: Apr. 2, 2015

(65) Prior Publication Data
US 2016/0287277 A1    Oct. 6, 2016

(51) Int. Cl.
A61B 17/22    (2006.01)

(52) U.S. Cl.
CPC ............ *A61B 17/22012* (2013.01); *A61B 2017/22014* (2013.01); *A61B 2017/22079* (2013.01)

(58) Field of Classification Search
CPC .......... A61B 17/2202; A61B 17/22012; A61B 17/22; A61B 17/320068; A61B 2017/22079; A61B 2017/22015; A61B 2017/22027
See application file for complete search history.

(56) References Cited

U.S. PATENT DOCUMENTS

| | | | |
|---|---|---|---|
| 3,433,226 A | 3/1969 | Boyd | |
| 3,872,472 A | 3/1975 | Moschgat | |
| 3,893,106 A | 7/1975 | Schulein | |
| 4,169,984 A | 10/1979 | Parisi | |
| 4,474,180 A | 10/1984 | Angulo | |
| 4,660,573 A | 4/1987 | Brumbach | |
| 4,886,491 A | 12/1989 | Parisi et al. | |
| 4,920,954 A | 5/1990 | Alliger et al. | |
| 4,933,918 A | 6/1990 | Landsrath et al. | |

(Continued)

FOREIGN PATENT DOCUMENTS

| | | |
|---|---|---|
| EP | 1025806 B1 | 4/2006 |
| WO | WO 99/44514 A1 | 9/1999 |

(Continued)

OTHER PUBLICATIONS

Office Action for U.S. Appl. No. 14/299,627, mailed Oct. 7, 2016.

(Continued)

*Primary Examiner* — Victor Nguyen

(57) ABSTRACT

An apparatus includes a transmission member having a proximal end portion and a distal end portion. The transmission member is configured to be inserted into a bodily lumen, and is configured to transfer ultrasonic energy from the proximal end portion to the distal end portion. The transmission member defines a lumen along a longitudinal center line of the transmission member. The distal end portion of the transmission member includes a concave engagement surface and a distal end surface. The distal end surface defines a plane that intersects the longitudinal center line of the transmission member at an angle of between about 75 degrees and about 105 degrees. The engagement surface is configured to engage a target tissue within the bodily lumen to limit movement of the target tissue along the longitudinal center line. The engagement surface defines an opening in fluid communication with the lumen.

17 Claims, 13 Drawing Sheets

(56) References Cited

U.S. PATENT DOCUMENTS

| | | | |
|---|---|---|---|
| 5,358,505 A | 10/1994 | Wuchinich | |
| 5,397,301 A | 3/1995 | Pflueger et al. | |
| 5,427,118 A | 6/1995 | Nita et al. | |
| 5,447,509 A | 9/1995 | Mills et al. | |
| 5,527,273 A | 6/1996 | Manna et al. | |
| 5,540,656 A | 7/1996 | Pflueger et al. | |
| 5,562,609 A | 10/1996 | Brumbach | |
| 5,630,837 A | 5/1997 | Crowley | |
| 5,674,235 A | 10/1997 | Parisi | |
| 5,720,710 A | 2/1998 | Tachibana et al. | |
| 5,735,280 A | 4/1998 | Sherman et al. | |
| 5,746,756 A | 5/1998 | Bromfield et al. | |
| 5,827,201 A | 10/1998 | Samson et al. | |
| 5,897,569 A | 4/1999 | Kellogg et al. | |
| 5,906,628 A | 5/1999 | Miyawaki et al. | |
| 5,989,275 A | 11/1999 | Estabrook et al. | |
| 6,050,971 A | 4/2000 | Garnier et al. | |
| 6,063,098 A | 5/2000 | Houser et al. | |
| 6,071,260 A | 6/2000 | Halverson | |
| 6,093,150 A | 7/2000 | Chandler et al. | |
| 6,165,163 A | 12/2000 | Chien et al. | |
| 6,217,543 B1 | 4/2001 | Anis et al. | |
| 6,274,963 B1 | 8/2001 | Estabrook et al. | |
| 6,296,620 B1 | 10/2001 | Gesswein et al. | |
| 6,299,591 B1 | 10/2001 | Banko | |
| 6,383,183 B1 | 5/2002 | Sekino et al. | |
| 6,450,975 B1 | 9/2002 | Brennan et al. | |
| 6,508,781 B1 | 1/2003 | Brennan et al. | |
| 6,511,478 B1 | 1/2003 | Burnside et al. | |
| 6,514,220 B2 | 2/2003 | Melton, Jr. et al. | |
| 6,524,299 B1 | 2/2003 | Tran et al. | |
| 6,577,042 B2 | 6/2003 | Lee et al. | |
| 6,617,760 B1 | 9/2003 | Peterson et al. | |
| 6,623,444 B2 | 9/2003 | Babaev | |
| 6,689,086 B1 | 2/2004 | Nita et al. | |
| 6,743,239 B1 | 6/2004 | Kuehn et al. | |
| 6,819,027 B2 | 11/2004 | Saraf | |
| 6,866,670 B2 * | 3/2005 | Rabiner | A61B 17/00234 606/114 |
| 6,942,677 B2 | 9/2005 | Nita et al. | |
| 7,089,063 B2 | 8/2006 | Lesh et al. | |
| 7,204,820 B2 | 4/2007 | Akahoshi | |
| 7,335,169 B2 | 2/2008 | Thompson et al. | |
| 7,335,180 B2 | 2/2008 | Nita et al. | |
| 7,371,235 B2 | 5/2008 | Thompson et al. | |
| 7,431,728 B2 | 10/2008 | Gerry et al. | |
| 7,494,467 B2 | 2/2009 | Makin et al. | |
| 7,494,468 B2 | 2/2009 | Rabiner et al. | |
| 7,503,895 B2 | 3/2009 | Rabiner et al. | |
| 7,682,366 B2 | 3/2010 | Sakurai et al. | |
| 7,955,293 B2 | 6/2011 | Nita et al. | |
| 8,052,607 B2 | 11/2011 | Byrd | |
| 8,062,566 B2 | 11/2011 | Nita et al. | |
| 8,115,366 B2 | 2/2012 | Hoffman et al. | |
| 8,133,236 B2 | 3/2012 | Nita | |
| 8,152,753 B2 | 4/2012 | Nita et al. | |
| 8,182,467 B2 | 5/2012 | Nguyen et al. | |
| 8,221,343 B2 | 7/2012 | Nita et al. | |
| 8,246,643 B2 | 8/2012 | Nita | |
| 8,308,677 B2 | 11/2012 | Nita et al. | |
| 8,585,724 B2 | 11/2013 | Palmer | |
| 8,721,581 B2 | 5/2014 | Zolli | |
| 9,173,667 B2 | 11/2015 | Du et al. | |
| 2002/0077550 A1 | 6/2002 | Rabiner et al. | |
| 2002/0077643 A1 | 6/2002 | Rabiner et al. | |
| 2003/0036705 A1 | 2/2003 | Hare et al. | |
| 2003/0065263 A1 | 4/2003 | Hare et al. | |
| 2003/0212333 A1 | 11/2003 | Rabiner et al. | |
| 2004/0127925 A1 | 7/2004 | Du et al. | |
| 2005/0085748 A1 | 4/2005 | Culp et al. | |
| 2006/0004396 A1 | 1/2006 | Easley et al. | |
| 2006/0090956 A1 | 5/2006 | Peshknvskiy et al. | |
| 2006/0116610 A1 | 6/2006 | Hare et al. | |
| 2007/0239027 A1 | 10/2007 | Nita | |
| 2008/0171965 A1 | 7/2008 | Soltani et al. | |
| 2008/0294051 A1 | 11/2008 | Koshigoe et al. | |
| 2008/0294087 A1 | 11/2008 | Steen et al. | |
| 2009/0018472 A1 | 1/2009 | Soltani et al. | |
| 2009/0082716 A1 | 3/2009 | Akahoshi | |
| 2010/0165793 A1 | 7/2010 | Haug | |
| 2010/0274269 A1 | 10/2010 | Song et al. | |
| 2010/0331871 A1 | 12/2010 | Nield et al. | |
| 2011/0004149 A1 | 1/2011 | Artsyukhovich et al. | |
| 2011/0015631 A1 | 1/2011 | Weiner et al. | |
| 2011/0046522 A1 | 2/2011 | Chan | |
| 2011/0213397 A1 | 9/2011 | Mathonnet | |
| 2011/0278988 A1 | 11/2011 | Young et al. | |
| 2011/0301506 A1 | 12/2011 | Volz | |
| 2012/0016272 A1 | 1/2012 | Nita et al. | |
| 2012/0157890 A1 | 6/2012 | Govari et al. | |
| 2012/0163126 A1 | 6/2012 | Campbell et al. | |
| 2012/0191115 A1 | 7/2012 | Gilbert | |
| 2012/0209303 A1 | 8/2012 | Frankhouser et al. | |
| 2012/0232435 A1 | 9/2012 | Nita et al. | |
| 2013/0253387 A1 | 9/2013 | Bonutti et al. | |
| 2014/0107534 A1 * | 4/2014 | Du | A61B 17/320068 601/2 |
| 2014/0128863 A1 | 5/2014 | Du et al. | |
| 2014/0364775 A1 | 12/2014 | Du et al. | |
| 2016/0022306 A1 | 1/2016 | Du et al. | |

FOREIGN PATENT DOCUMENTS

| | | |
|---|---|---|
| WO | WO 00/62688 | 10/2000 |
| WO | WO 2005/072391 A2 | 8/2005 |
| WO | WO 2006/059966 A1 | 6/2006 |
| WO | WO 2012/118018 A1 | 9/2012 |

OTHER PUBLICATIONS

Extended European Search Report for European Application No. 14811292, maiied Dec. 14, 2016.

"Design Considerations in Small-Diameter Medical Tubing," Jan. 1, 2001 [online] [Retrieved from the Internet] Retrieved from http://www.mddio9nline.com/print/181, Retrieved on Sep. 21, 2012.

Cyberwand™, Dual Probe Ultrasonic Lithotripter System, Cybersonics, Inc.

"Fundamentals of Ultrasonic Imaging and Flaw Detection," National Instruments tutorial, Feb. 11, 2010.

"Pebax® Tubing Grades," Applied Medical Tubing [online] [Retrieved from the Internet] Retrieved on www.appliedtubing.com/_mgxroot/page_10795.html, Retrieved on Nov. 1, 2012.

Pagnani, C. et al., "Prevention of stone migration with the Accordion during endoscopic ureteral lithotripsy," J Endourology, 26(5):484-488 (May 2012).

International Search Report and Written Opinion in PCT/US2014/041520 mailed Oct. 29, 2014.

* cited by examiner

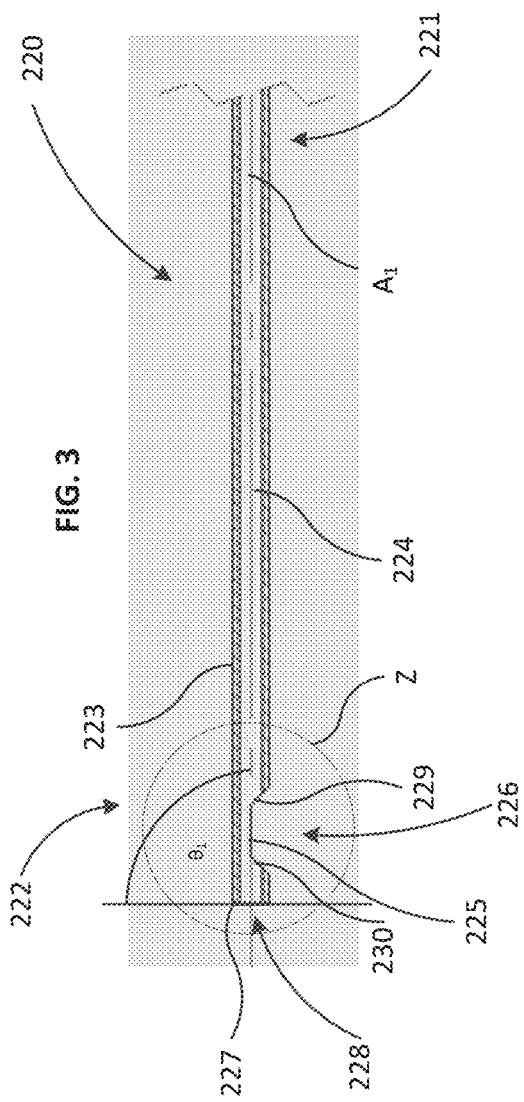

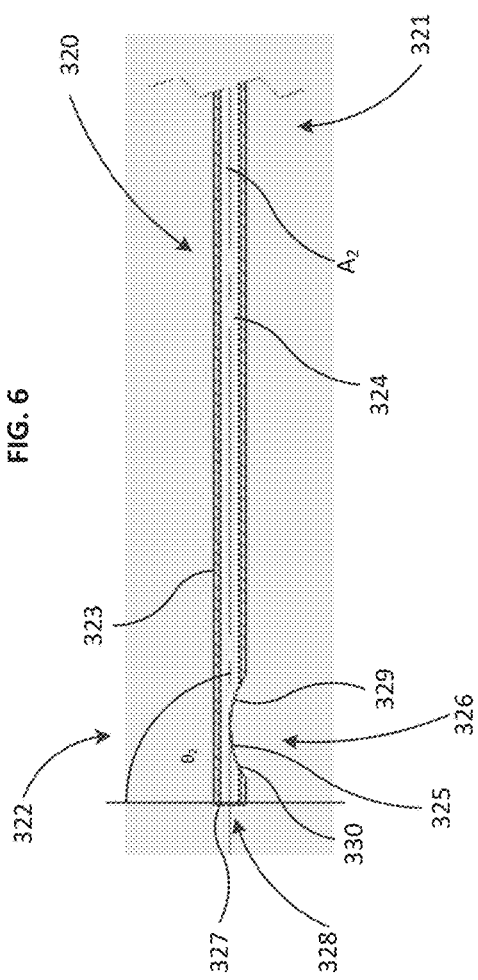

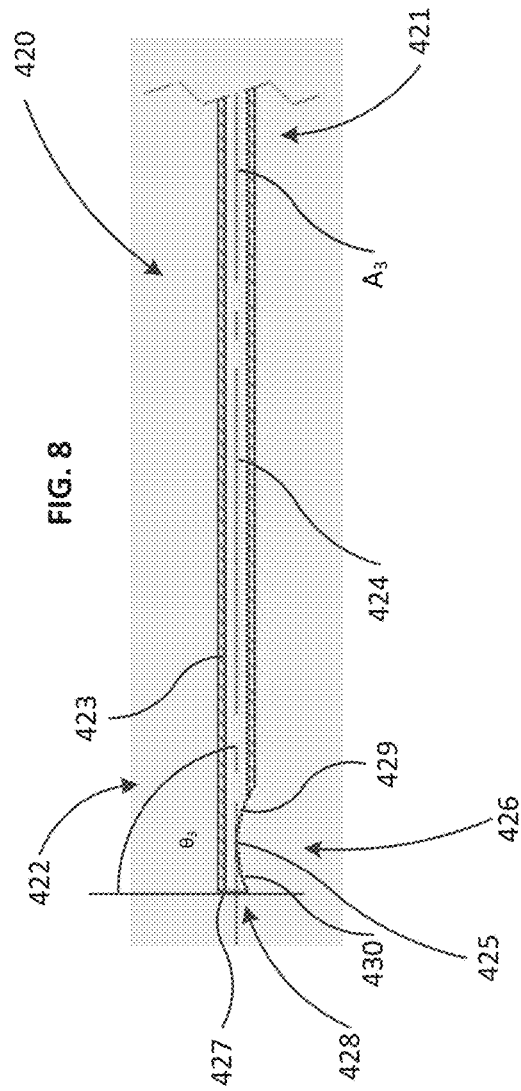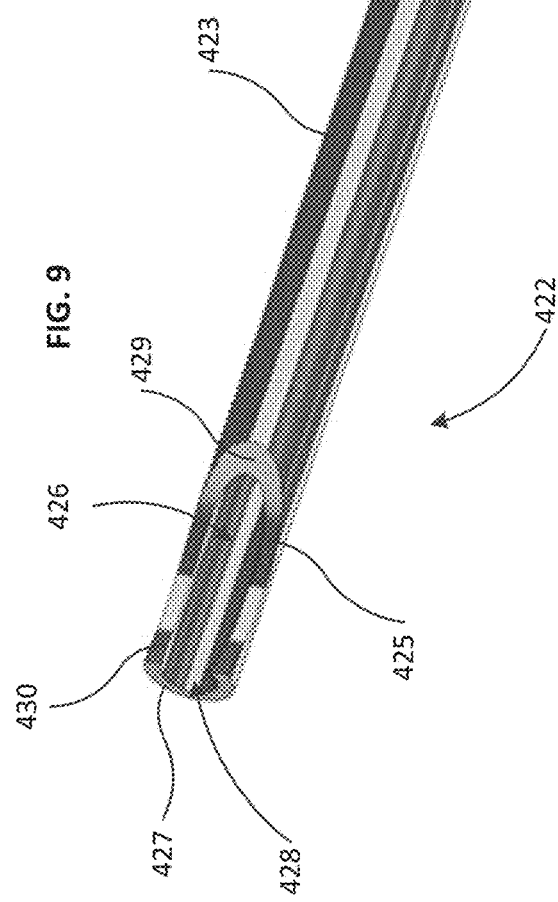

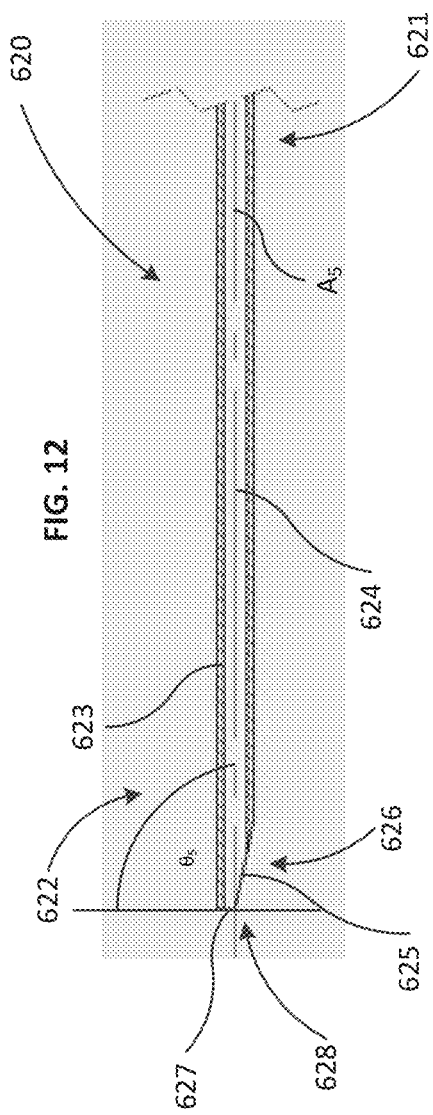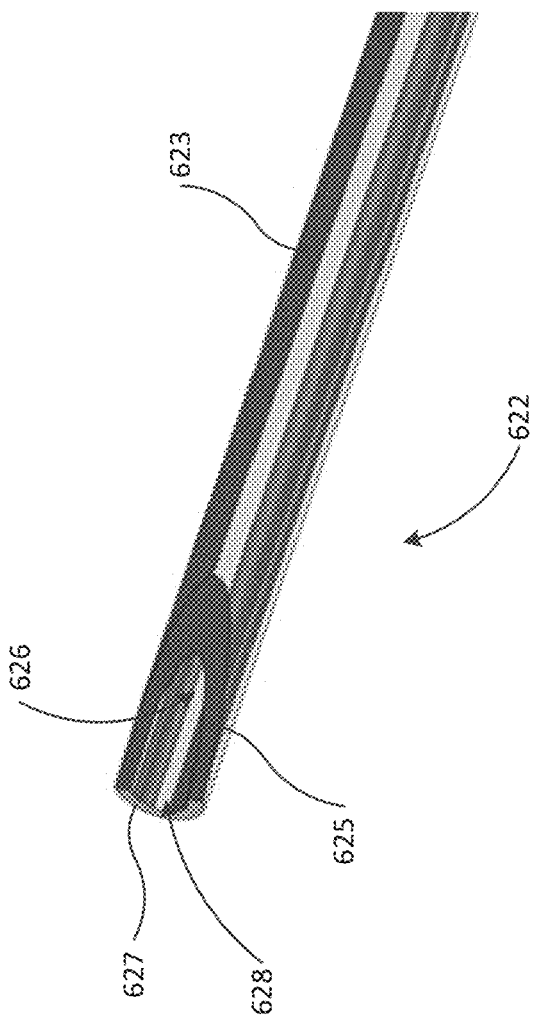

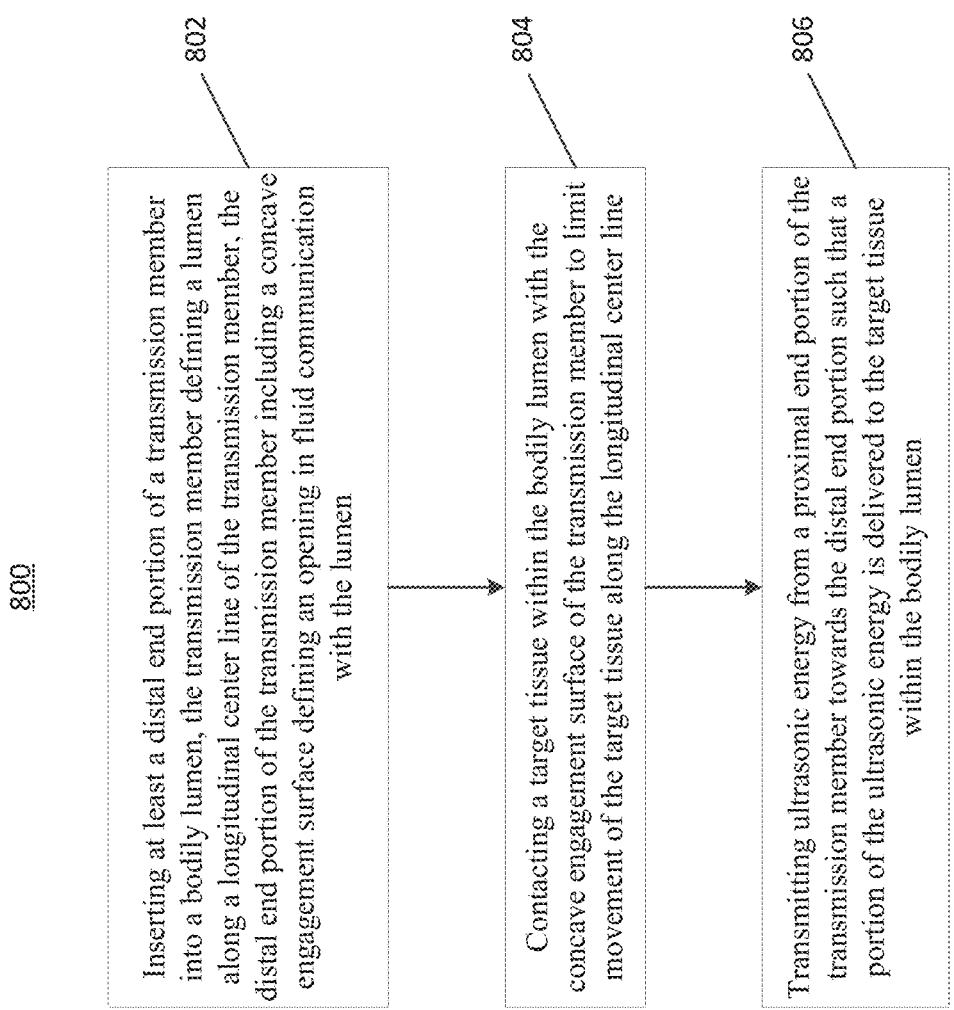

FIG. 16
800

802 — Inserting at least a distal end portion of a transmission member into a bodily lumen, the transmission member defining a lumen along a longitudinal center line of the transmission member, the distal end portion of the transmission member including a concave engagement surface defining an opening in fluid communication with the lumen 804 — Contacting a target tissue within the bodily lumen with the concave engagement surface of the transmission member to limit movement of the target tissue along the longitudinal center line 806 — Transmitting ultrasonic energy from a proximal end portion of the transmission member towards the distal end portion such that a portion of the ultrasonic energy is delivered to the target tissue within the bodily lumen

DEVICES AND METHODS FOR REMOVING OCCLUSIONS FROM A BODILY CAVITY

BACKGROUND

The embodiments described herein relate generally to a device used in conjunction with an ultrasonic ablation device, and, more specifically, to a transmission member configured to transfer ultrasonic energy to a bodily tissue (including an occlusion, kidney stone or the like) from an ultrasonic energy source.

Known ultrasonic energy transmission systems are used in many different medical applications, such as, for example, for medical imaging, to disrupt obstructions and/or to ablate bodily tissue. In known ultrasonic energy transmission systems for tissue ablation, ultrasonic energy is transferred from an ultrasonic energy source through a transducer horn and then a transmission member, such as a wire, to a distal head. Ultrasonic energy propagates through the transmission member as a periodic wave thereby causing the distal head to vibrate. Such vibrational energy can be used to ablate or otherwise disrupt bodily tissue, for example, a vascular obstruction, a calculus, such as a kidney stone, or the like.

Some known devices for the removal of a calculus include an ultrasonic probe (or transmission member) used to apply ultrasonic energy for fragmentation and removal of the calculus. In some known methods, the ultrasonic probe is placed into contact with the calculus (in the urinary tract, for example) and is then used to deliver ultrasonic energy to fragment the calculus. The calculus fragments are then aspirated out of the body through a lumen of the probe. However, the calculus and calculus fragments often clog the opening of the lumen. Additionally, it can be difficult to maintain contact between the distal end of the probe and the calculus, reducing the efficiency of the ultrasonic energy delivery. Moreover, the failure to maintain the position of the calculus can also result in proximal (or "backward") migration of the calculus and/or fragments thereof. For example, known methods of ablating a calculus within the ureter can produce migration of the calculus towards the kidney, which can necessitate additional procedures.

Some known devices have attempted to solve the problem of the lumen clogging during aspiration by defining a slot or secondary opening extending from the primary lumen opening. In such arrangements, smaller calculus fragments can be aspirated through the slot even if the primary opening is clogged. Even with these designs, however, it remains difficult to control the location of a calculus relative to the probe openings, and so the fragmentation remains inefficient, and the possibility of undesirable migration of the calculus and fragments exists.

Some known devices for the disruption of bodily tissue include a basket for maintaining the position of and retrieving a calculus from a bodily lumen. For example, some known procedures for removing calculi in the ureter include placing a small tube, known as a ureteroscope, in the ureter. Next, a basket is extended from the ureteroscope and collects the calculus. Optionally, if the calculus is large it can be fragmented using, for example, a laser device, ultrasonic device or the like. Finally, the ureteroscope, the basket, and the calculus are removed from the ureter. However, this process can be time consuming and can require complicated manipulations with the instrument.

Some known devices for breaking up bodily occlusions include sharp distal ends. However, unlike in vascular procedures where a sharp tip may be desirable to break up or pass through an occlusion, sharp tips should be avoided in ureteral procedures. Sharp tips have a high risk of puncturing the ureter. Additionally, calculi within the ureter (i.e., kidney stones) are not usually able to be broken up by sharp probe tips.

Thus, there is a need for improved devices for ablating an occlusion that can limit the movement of the calculi during the procedure.

SUMMARY

Devices and methods of ablating and/or removing bodily occlusions are described herein. In some embodiments, an apparatus includes a transmission member having a proximal end portion and a distal end portion. The transmission member is configured to be inserted into a bodily lumen, and is configured to transfer ultrasonic energy from the proximal end portion to the distal end portion. The transmission member defines a lumen along a longitudinal center line of the transmission member. The distal end portion of the transmission member includes a concave engagement surface and a distal end surface. The distal end surface defines a plane that intersects the longitudinal center line of the transmission member at an angle of between about 75 degrees and about 105 degrees. The engagement surface is configured to engage a target tissue within the bodily lumen to limit movement of the target tissue along the longitudinal center line. The engagement surface defines an opening in fluid communication with the lumen.

BRIEF DESCRIPTION OF THE DRAWINGS

FIG. 3 is a cross-sectional side view of a transmission member, according to an embodiment.

FIG. 4 is a side perspective view of the transmission member shown in FIG. 3.

FIG. 6 is a cross-sectional side view of a transmission member, according to an embodiment.

FIG. 7 is a side perspective view of the transmission member shown in FIG. 6.

FIG. 8 is a cross-sectional side view of a transmission member, according to an embodiment.

FIG. 9 is a side perspective view of the transmission member shown in FIG. 8.

FIG. 12 is a cross-sectional side view of a transmission member, according to an embodiment.

FIG. 13 is a side perspective view of the transmission member shown in FIG. 12.

FIG. 16 is a flow chart of a method, according to an embodiment.

DETAILED DESCRIPTION

Figure 1:
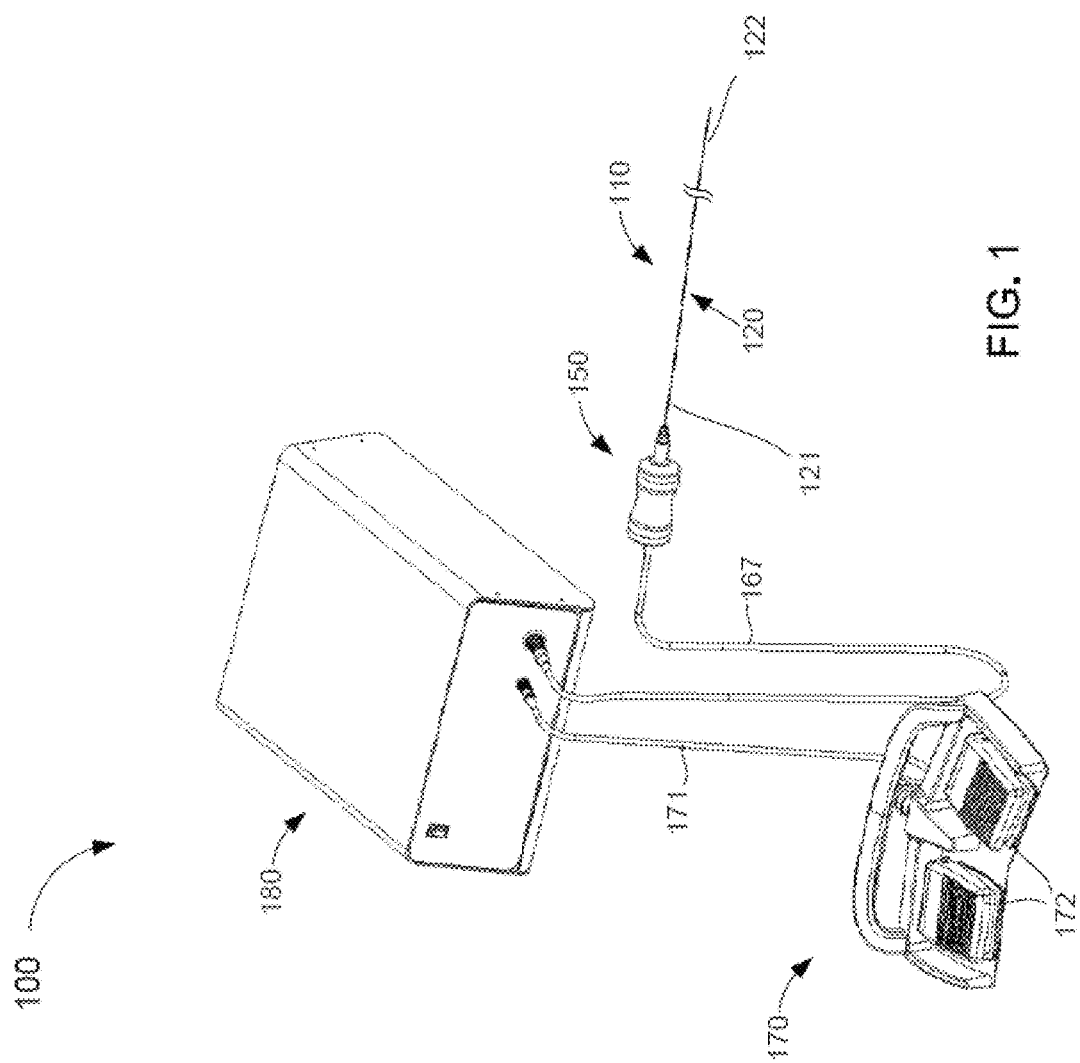
FIG. 1 is an illustration of a system for delivering ultrasonic energy to a bodily tissue according to an embodiment.

Devices and methods of ablating and/or removing bodily occlusions are described herein. In some embodiments, an apparatus includes a transmission member having a proximal end portion and a distal end portion. The transmission member is configured to be inserted into a bodily lumen, and is configured to transfer ultrasonic energy from the proximal end portion to the distal end portion. The transmission member defines a lumen along a longitudinal center line of the transmission member. The distal end portion of the transmission member includes a concave engagement surface and a distal end surface. The distal end surface defines a plane that intersects the longitudinal center line of the transmission member at an angle of between about 75 degrees and about 105 degrees. The engagement surface is configured to engage a target tissue within the bodily lumen to limit movement of the target tissue along the longitudinal center line. The engagement surface defines an opening in fluid communication with the lumen.

In some embodiments, an apparatus includes a transmission member having a proximal end portion and a distal end portion. The transmission member is configured to be inserted into a bodily lumen, and is configured to transfer ultrasonic energy from the proximal end portion to the distal end portion. The transmission member defines a lumen along a longitudinal center line of the transmission member. The distal end portion of the transmission member includes an engagement surface and a distal end surface. The distal end surface defines a plane that intersects the longitudinal center line of the transmission member at an angle of between about 75 degrees and about 105 degrees. The engagement surface intersects the distal end surface and is configured to engage a target tissue within the bodily lumen to limit movement of the target tissue along the longitudinal center line. The engagement surface defines an opening in fluid communication with the lumen.

In some embodiments, an apparatus includes a transmission member and a sheath. The transmission member has a proximal end portion and a distal end portion. The transmission member is configured to be inserted into a bodily lumen, and is configured to transfer ultrasonic energy from the proximal end portion to the distal end portion. The transmission member defines a lumen along a longitudinal center line of the transmission member. The distal end portion of the transmission member includes a first engagement surface. The first engagement surface defines an opening in fluid communication with the lumen. The sheath is configured to be movably disposed about at least the distal end portion of the transmission member. The sheath defines a second engagement surface. The first engagement surface and the second engagement surface are configured to engage a target tissue within the bodily lumen to limit movement of the target tissue along the longitudinal center line of the transmission member.

In some embodiments, a method includes inserting at least a distal end portion of a transmission member into a bodily lumen. The transmission member defines a lumen along a longitudinal center line of the transmission member. The distal end portion of the transmission member includes a concave engagement surface defining an opening in fluid communication with the lumen. A target tissue is contacted within the bodily lumen with the concave engagement surface of the transmission member to limit movement of the target tissue along the longitudinal center line. Ultrasonic energy is transmitted from a proximal end portion of the transmission member towards the distal end portion such that a portion of the ultrasonic energy is delivered to the target tissue within the bodily lumen.

In some embodiments, a method includes inserting at least a distal end portion of an ablation assembly into a bodily lumen. The ablation assembly includes a transmission member and a sheath disposed about at least a distal end portion of the transmission member. The transmission member defines a lumen along a longitudinal center line of the transmission member. The distal end portion of the transmission member includes an engagement surface defining an opening which is in fluid communication with the lumen. The sheath is moved relative to the transmission member to place an engagement surface of the sheath distal to a target tissue within the bodily lumen. The target tissue is contacted with the engagement surface of the transmission member and the engagement surface of the sheath to limit movement of the target tissue along the longitudinal center line. Ultrasonic energy is then transmitted from a proximal end portion of the transmission member towards the distal end portion of the transmission member such that a portion of the ultrasonic energy is delivered to the target tissue within the bodily lumen.

As used in this specification, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used herein, the term "target tissue" refers to an internal or external tissue of or within a patient to which ultrasonic energy ablation techniques are applied. For example, a target tissue can be cancer cells, tumor cells, lesions, vascular occlusions, thrombosis, calculi, uterine fibroids, bone metastases, adenomyosis, or any other bodily tissue. Furthermore, the presented examples, of target tissues are not an exhaustive list of suitable target tissues. Thus, the ultrasonic energy systems described herein are not limited to the treatment of the aforementioned tissues and can be used on any suitable bodily tissue. Moreover, a "target tissue" can also include an artificial substance within or associated with a body, such as for example, a stent, a portion of an artificial tube, a fastener within the body or the like. Thus, for example, the ultrasonic energy systems described herein can be used on or within a stent or artificial bypass graft.

The embodiments described herein relate to ultrasonic energy ablation systems. In such systems a transmission member can be operably coupled to an ultrasonic energy source to deliver ultrasonic energy to a target bodily tissue. For example, FIG. 1 is an illustration of an ultrasonic energy ablation system 100, according to an embodiment. The ultrasonic energy ablation system 100 (also referred to herein as "ultrasonic system" or simply "system") includes an ultrasonic generator 180, a foot switch 170, an ultrasonic transducer assembly 150, and a probe assembly 110. The ultrasonic generator 180 (or "generator") can be any suitable generator configured to generate, control, amplify, and/or transfer an electric signal (e.g., a voltage) to the transducer assembly 150.

The ultrasonic generator 180 includes at least a processor, a memory and the circuitry (not shown in FIG. 1) to produce an electronic signal (i.e., a current and a voltage) having the desired characteristics that can be received by the ultrasonic transducer assembly 150 and converted into ultrasonic energy. In some embodiments, the ultrasonic generator 180 can be electrically coupled to (e.g., "plugged into") an electric receptacle such that the ultrasonic generator 180 receives a flow of electric current. For example, in some embodiments, the ultrasonic generator 180 can be plugged into a wall outlet that delivers alternating current (AC) electrical power at a given voltage (e.g., 120V, 230V, or other suitable voltage) and a given frequency (e.g., 60 Hz, 50 Hz, or other suitable frequency).

Although not shown in FIG. 1, the ultrasonic generator 180 includes the electronic circuitry, hardware, firmware and or instructions to cause the ultrasonic generator 180 to act as a frequency inverter and/or voltage booster. In this manner, the ultrasonic generator 180 can produce and/or output a voltage to the transducer assembly 150 having the desired characteristics to produce the desired ultrasonic energy output. For example, in some embodiments, the ultrasonic generator 180 can receive AC electrical power at a frequency of approximately 60 Hz and a voltage of approximately 120V and convert the voltage to a frequency up to approximately 20,000 Hz to 35,000 Hz with a voltage of approximately 500-1500 VAC (RMS). Thus, the ultrasonic generator 180 can supply the transducer assembly 150 with a flow of AC electrical power having an ultrasonic frequency.

As shown in FIG. 1, the system 100 includes the foot switch 170 that is in electric communication with the ultrasonic generator 180 via a foot switch cable 171. The foot switch 170 includes a set of pedals 172 (e.g., two pedals as shown) that are operative in controlling the delivery of the ultrasonic electrical energy supplied to the ultrasonic transducer assembly 150. For example, in some embodiments, a user (e.g., a physician, technician, etc.) can engage and/or depress one or more of the pedals 172 to control the current supplied to the ultrasonic transducer assembly 150 such that, in turn, the probe assembly 110 delivers the desired ultrasonic energy to the bodily tissue, as further described in detail herein.

The transducer assembly 150 is in electric communication with the ultrasonic generator 180 via a transducer cable 167. In this manner, the transducer assembly 150 can receive an electrical signal (i.e., voltage and current) from the ultrasonic generator 180. The transducer assembly 150 is configured to produce and amplify the desired ultrasonic energy via a set of piezoelectric members 162 (i.e., piezoelectric rings) and an ultrasonic horn 163 (see e.g., FIG. 2), and transfer the ultrasonic energy to the probe assembly 110 and/or the transmission member 120. The transducer assembly 150 can be any suitable assembly of the types shown and described herein.

Figure 2:
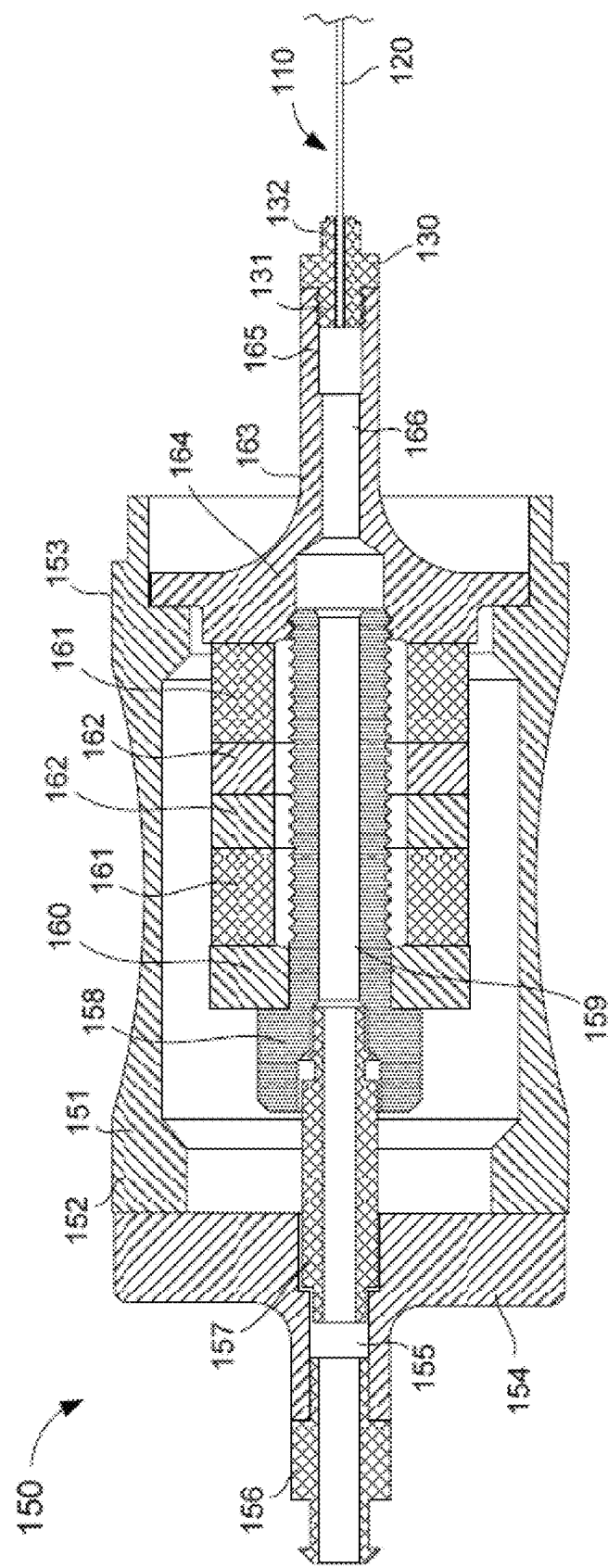
FIG. 2 is a cross-sectional view of an ultrasonic transducer included in the system of FIG. 1.

For example, in some embodiments, as shown in FIG. 2, the transducer assembly 150 includes a housing 151 having a proximal end portion 152 and a distal end portion 153. The housing 151 is configured to house or otherwise enclose at least a portion of a flow tube 157, a bolt 158, a back plate 160, a set of insulators 161, a set of piezoelectric rings 162, and a transducer horn 163.

The proximal end portion 152 of the housing 151 is coupled to a proximal cover 154 (e.g., via an adhesive, a press or friction fit, a threaded coupling, a mechanical fastener, or the like). The proximal cover 154 defines an opening 155 such that the proximal cover 154 can receive a portion of a connector 156 (e.g., a luer connector) on a proximal side thereof (e.g., substantially outside the housing 151) and a portion of the flow tube 157 on a distal side thereof (e.g., substantially inside the housing 151). Expanding further, the proximal cover 154 can receive the connector 156 and the flow tube 157 such that the proximal cover 154 forms a substantially fluid tight seal with the connector 156 and the flow tube 157. In this manner, a vacuum can be applied via the connector 156 to irrigate and/or aspirate the region of the body within which the probe assembly 110 is disposed. Similarly stated, this arrangement results in the connector 156 being placed in fluid communication with the lumen 122 defined by the transmission member 120.

The distal end portion 153 of the housing 151 is configured to receive the transducer horn 163 such that the transducer horn 163 is coupled to an inner surface of the housing 151. More specifically, the transducer horn 163 can be disposed at least partially within the housing 151 such that the transducer horn 163 can be moved relative to the housing 151 (e.g., when amplifying the ultrasonic energy), but not moved out of the housing 151 during normal use. The transducer horn 163 includes a proximal end portion 164 and a distal end portion 165 and defines a lumen 166 therethrough. The lumen 166 is configured to receive a portion of the bolt 158 at the proximal end portion 164 of the transducer horn 163 and a portion of the probe assembly 120 at the distal end portion 165 of the transducer horn 163, both of which are described in further detail herein.

As shown in FIG. 2, the back plate 160, the insulators 161, and the piezoelectric rings 162 are disposed within the housing 151 and about the bolt 158. More specifically, the arrangement of the back plate 160, the insulators 161, and the piezoelectric rings 162 is such that the back plate 160 is disposed proximal to the insulators 161 and the piezoelectric rings 162. The piezoelectric rings 162 are each disposed between the insulators 161. Similarly stated, a first insulator 161 is disposed proximal to the piezoelectric rings 162 and a second insulator 161 is disposed distal to the piezoelectric rings 162. The piezoelectric rings 162 are in electric communication (e.g., via wires not shown in FIGS. 1 and 2) with the ultrasonic generator 180, as described in further detail herein.

As shown in FIG. 2, a portion of the bolt 158 is configured to be disposed within the lumen 166 defined by the transducer horn 163. More specifically, the portion of the bolt 158 forms a threaded fit with an inner surface of the transducer horn 163 that defines the lumen 166. In this manner, the bolt 158 can be advanced within the lumen 166 such that the bolt 158 exerts a compressive force on the backing plate 160, the insulators 161, and the piezoelectric rings 162. Thus, the backing plate 160, the insulators 161, and the piezoelectric rings 162 are retained between a head of the bolt 158 (e.g., at the proximal end) and a proximal surface of the transducer horn 163. The torque applied to the bolt and/or the clamping force exerted between the head of the bolt 158 and the proximal surface of the transducer horn 163 is such that that the deviation of the transducer natural frequency deviation is within ten percent from nominal Therefore, in use, the piezoelectric rings 162 can vibrate and/or move the transducer horn 163, as further described herein.

The bolt 158 further defines a lumen 159 such that a proximal end portion of the bolt 158 can receive a distal end portion of the flow tube 157. In this manner, the lumen 159 defined by the bolt 158 and the flow tube 157 collectively place the lumen 166 defined by the transducer horn 163 in fluid communication with the connector 156. Thus, the lumen 166 of the transducer horn 163 can be placed in fluid communication with a volume substantially outside of the proximal end of the housing 151.

As shown in FIGS. 1 and 2, the probe assembly 110 includes at least a transmission member 120 and a coupler 130. The coupler 130 includes a proximal end portion 131 and a distal end portion 132 and defines a lumen (not identified in FIG. 2) that extends therethrough. The proximal end portion 131 of the coupler 130 is disposed within the lumen 166 at the distal end portion 165 of the transducer horn 163 and forms a threaded fit with the inner surface of the transducer horn 163 that defines the lumen 166. The distal end portion 131 of the coupler 130 is configured to receive a portion of the transmission member 120 to fixedly couple the transmission member 120 to the coupler 130. In this manner, the probe assembly 110 can be removably coupled to the transducer assembly 150 via the coupler 130. Although the probe assembly 110 is shown as including the coupler 130, in other embodiments, the probe assembly 110 or any of the probe assemblies herein can include any suitable coupler. For example, in some embodiments, any of the probe assemblies herein can include any of the couplers shown and described in U.S. Patent Publication No. 2014/0364775, entitled "Systems and Methods for Delivering Ultrasonic Energy to a Bodily Tissue" (the '775 Publication), which is incorporated herein by reference in its entirety.

The transmission member 120 is an elongate tube having a proximal end portion 121 and a distal end portion 122. The transmission member 120 can be any suitable shape, size, or configuration and is described in further detail herein with respect to specific embodiments. In some embodiments, the transmission member 120 can be configured to facilitate the passage of the transmission member 120 through a bodily lumen (e.g., a urinary tract, a vein, artery, etc.). For example, in some embodiments, a portion of the transmission member 120 can be formed from a material of lower stiffness than a different portion of the transmission member 120 formed from a material of greater stiffness. In some embodiments, the transmission member 120 can optionally include any suitable feature configured to limit movement (or migration) of a target tissue within a bodily lumen of a patient (e.g., a urinary tract, a vein, artery, etc.). For example, in some embodiments, the transmission member 120 can include a concave engagement surface configured to engage a target tissue within a bodily lumen to limit movement of the target tissue along the longitudinal center line, as described herein with respect to specific embodiments. In some embodiments, the transmission member 120 can include a blunt distal end surface defining a plane that intersects a longitudinal center line at an angle of between about 75 degrees and about 105 degrees and an engagement surface configured to engage a target tissue within a bodily lumen to limit movement of the target tissue along the longitudinal center line, as described herein with respect to specific embodiments.

In use, a user (e.g., a surgeon, a technician, physician, etc.) can operate the ultrasonic system 100 to deliver ultrasonic energy to a target bodily tissue within a patient. The user can, for example, engage the pedals 172 of the foot switch 170 such that the ultrasonic generator 180 generates an alternating current (AC) and voltage with a desired ultrasonic frequency (e.g., 20,000 Hz). In this manner, the ultrasonic generator 180 can supply AC electric power to the piezoelectric rings 162. The AC electric power can urge the piezoelectric rings 162 to oscillate (e.g., expand, contract, or otherwise deform) at the desired frequency, which, in turn, causes the transducer horn 163 to move relative to the housing 151. Thus, with the probe assembly 110 coupled to the transducer horn 163, the movement of the transducer horn 163 vibrates and/or moves the probe assembly 110. In this manner, the distal end portion 122 of the transmission member 120 can be disposed within the patient adjacent to a target tissue such that the transmission member 120 transfers at least a portion of the ultrasonic energy to the target tissue (not shown in FIGS. 1 and 2). For example, in some embodiments, a distal tip of the transmission member 120 can impact a target tissue such as, for example, to break apart the occlusion. In some embodiments, the movement of the distal end portion 122 of the transmission member 120 is such that cavitations occur within the portion of the patient. In this manner, the cavitations can further break apart a target tissue. In some embodiments, the ultrasonic system 100 can optionally be used to aspirate and/or to supply irrigation to a target tissue site.

While described above in a general way, an ultrasonic energy system, such as the ultrasonic energy system 100, can include any suitable probe or transmission member of the types shown herein having any engagement surface suitable for limiting movement of a target tissue. For example, in some embodiments, a transmission member can have a concave engagement surface that can limit the movement of a target tissue within a bodily lumen. In some embodiments, the bodily lumen can be a ureter and the target tissue can be a calculus (or "stone"). In such embodiments, the concave engagement surface can be configured to limit migration of the calculus or portions thereof back towards the kidney. For example, FIGS. 3 and 4 show a transmission member 220, according to an embodiment. The transmission member 220 can be included in any suitable ultrasonic energy system shown and described herein, such as, for example, the system 100 described above with reference to FIGS. 1 and 2. The transmission member 220 is an elongate member including a side wall 223 and defining a lumen 224 along a longitudinal center line $A_1$. The transmission member 220 can provide aspiration from and/or irrigation to a target tissue site during an ultrasonic procedure (via the lumen 224, and the connecting lumens of any component to which the transmission member 220 is coupled).

As shown in FIG. 3, transmission member 220 includes a proximal end portion 221 and a distal end portion 222. The proximal end portion 221 can be at least operably coupled to an ultrasonic energy source such as the ultrasonic generator 180 and/or the transducer assembly 150 described above. For example, in some embodiments, the proximal end portion 221 can be disposed within a lumen of a coupler, such as coupler 130 described above with reference to FIG. 2, or any of the couplers described in the '775 Publication. In such embodiments, the coupler can be coupled to the ultrasonic energy source 180, thus, operably coupling the transmission member 220 to the ultrasonic energy source 180.

The distal end portion 222 can be disposed within a body to transfer ultrasonic energy from the proximal end portion 221 to a bodily tissue. For example, in some embodiments, the distal end portion can be disposed within a ureter, and can be used to remove a calculus therein, as described below. The distal end portion 222 of the transmission member 220 includes a distal end surface 227 and an engagement surface 225. The distal end surface 227 is devoid of sharp edges and/or is blunt. More particularly, the distal end surface 227 defines a plane that intersects the longitudinal center line $A_1$ at an angle $\theta_1$ of about 90 degrees. In this manner, the likelihood that the distal end surface 227 will perforate, tear or pierce the wall defining the bodily lumen is limited. Although shown as being about 90 degrees, in other embodiments, the distal end surface is between about 75 degrees and about 105 degrees. The distal end surface 227 defines a distal end opening 228 in fluid communication with the lumen 224 of the transmission member 220. The distal end opening 228 can be configured for the aspiration and/or irrigation of a target tissue site via the lumen 224.

Figure 5:
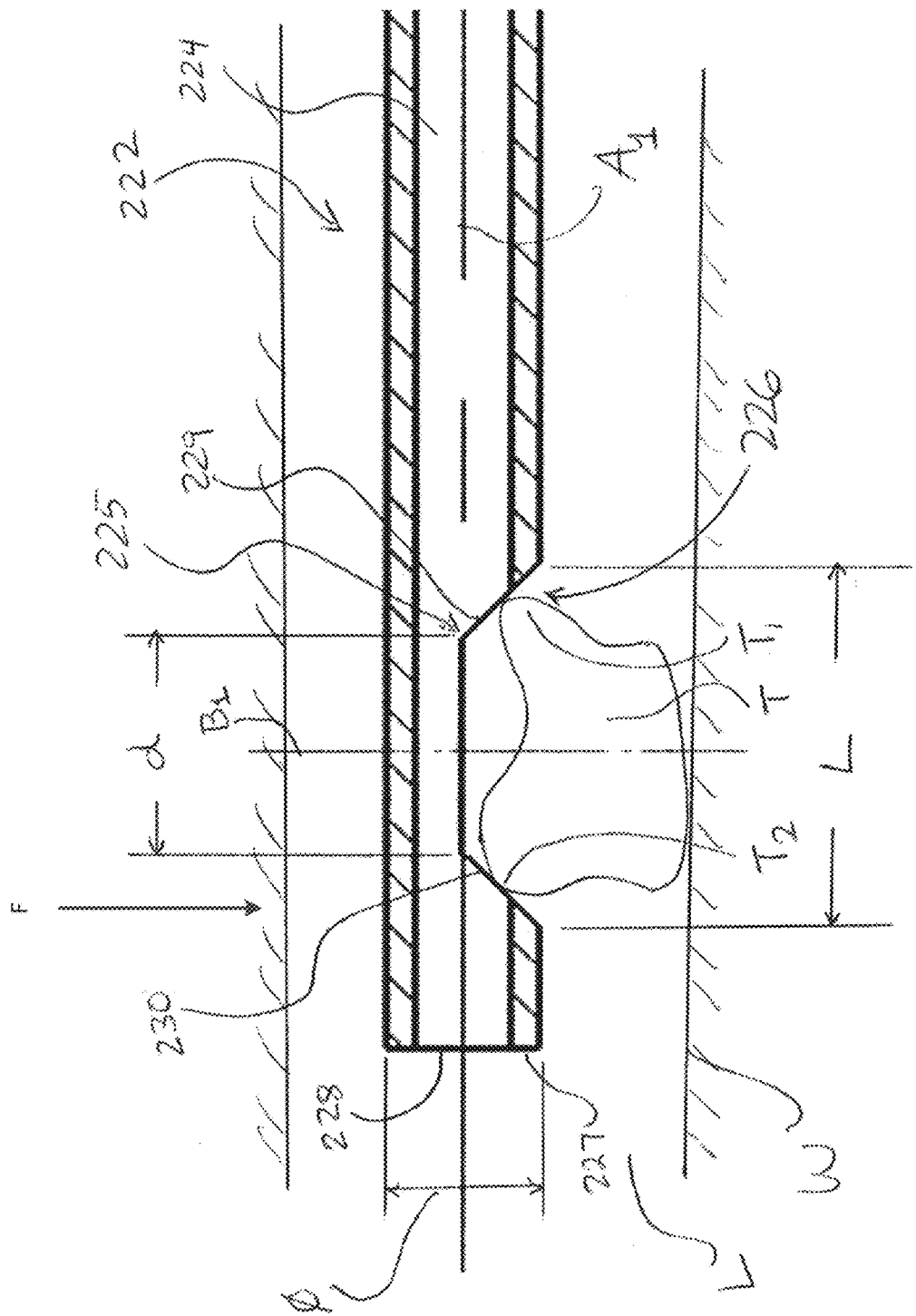
FIG. 5 is an enlarged view of the portion of the transmission member of FIG. 3 shown in the region marked Z.

FIG. 5 shows the distal end portion 222 of the transmission member 220 disposed within a bodily lumen L (e.g., a ureter), and in contact with a target tissue T (e.g., a calculus). As shown, the engagement surface 225 of the distal end portion 222 of the transmission member 220 is concave and is configured to engage at least a portion of a target tissue within the bodily lumen to limit movement of the target tissue along the longitudinal center line $A_1$. As a result of being concave, the engagement surface 225 is capable of limiting the movement of a target tissue in both directions along the longitudinal center line $A_1$. In particular, as shown in FIG. 5, the engagement surface 225 includes a first portion 229 and a second portion 230 that is opposite from first portion 229. In use, the first portion 229 is configured to engage a first side $T_1$ of a target tissue T and the second portion 230 is configured to engage a second side $T_2$ of the target tissue T. In this manner, both the distal and proximal movement of the target tissue T within the bodily lumen L is limited.

In use, a lateral force F can be applied to the transmission member 220 to press the engagement surface 225 against the target tissue T (e.g., a kidney stone or the like), as shown by the arrow F. The lateral force F can cause the engagement surface 225 to move the target tissue into contact with a wall W defining the bodily lumen L. Continued application of the lateral force F can maintain the target tissue T in a position between the engagement surface 225 and the wall W. The proximal end portion 221 of the transmission member 220 can transmit ultrasonic energy towards the distal end portion 222 such that a portion of the ultrasonic energy is delivered to the target tissue T. The target tissue T can absorb the ultrasonic energy, causing the target tissue T to break into smaller portions. Because the target tissue T can be held in place relative to the transmission member 220 and/or the wall W, the delivery of ultrasonic energy to the target tissue T will result in the target tissue T breaking apart faster than if the target tissue T is freely movable relative to the transmission member 220 and/or the wall W. Additionally, because the engagement surface 225 can engage the target tissue T and hold the target tissue T in place relative to the transmission member 220, the amount of movement of the transmission member 220 needed to maintain contact between the transmission member 220 and the target tissue T for the delivery of ultrasonic energy will be reduced. The decreased amount of movement of the transmission member 220 reduces the likelihood that the transmission member will damage the wall W of the bodily lumen L. When the ultrasonic energy has broken the target tissue T into portions small enough to be able to move through the lumen 224 of the transmission member 220, the portions of the target tissue T can be aspirated through the lumen 224.

The engagement surface 225 defines an opening 226 in fluid communication with the lumen 224. In this manner, portions of the target tissue T can be aspirated via the lumen 224 through the opening 226. Moreover, as shown in FIGS. 3-5, the engagement surface 225 can be spaced apart from the distal end surface 227. For example, in some embodiments, a distance d between the first portion 229 and the second portion 230 is less than about four times a diameter $\phi$ of the distal end portion 222 of the transmission member 220. In some embodiments, a length L of the opening 226 along the longitudinal center line $A_1$ is less than about four times the diameter $\phi$ of the distal end portion 222 of the transmission member 220.

The first portion 229 and the second portion 230 of the engagement surface 225 are configured to engage, retain and/or surround the target tissue to facilitate the ablation thereof. For example, as shown in FIG. 5, in some embodiments, a slope of the first portion 229 and a slope of the second portion 230 are symmetrical about an axis $B_1$ (that is normal to the longitudinal center line $A_1$). The slope of the first portion 229 can be negative and the slope of the second portion 230 can be positive. In this manner, the shape of the engagement surface 225 can prevent both distal (or backward) migration of the target tissue T (i.e., by engagement with the positive-sloped second portion 230) and proximal (or forward) migration of the target tissue T (i.e., by engagement with the negative-sloped first portion 229). As a result, the lumen 224 of the transmission member 220 has a reduced likelihood of being obstructed by the target tissue T because the target tissue T is retained by the engagement surface 225 and the distal end opening 228 remains open. The engagement surface 225 can hold the target tissue T in the opening 226 in a position that leaves the distal end opening 228 unobstructed and the lumen 224 at least partially unobstructed along the entire length of the lumen 224. Therefore, the aspiration through the lumen 224 can be maintained when the target tissue T is engaged with the engagement surface 225, even if the opening 226 is obstructed or partially obstructed by the target tissue T. As the target tissue T is broken into smaller portions by the application of ultrasonic energy, the smaller portions can be aspirated through the opening 226 or the distal end opening 228. Although shown as symmetrical about the axis $B_1$, in other embodiments the slope of the first portion 229 and the slope of the second portion 230 can be parallel or asymmetrical.

As shown in FIGS. 3-5, the engagement surface 225 can include intersecting discontinuous edges (i.e., the first portion 229 and the second portion 230). In other embodiments, the engagement surface can be substantially continuous. For example, FIGS. 6 and 7 show a transmission member 320 having a continuous and curved engagement surface 325. The transmission member 320 can be included in any suitable ultrasonic energy system shown and described herein, such as, for example, the system 100 described above with reference to FIGS. 1 and 2. The transmission member 320 is an elongate member including a side wall 323 and defining a lumen 324 along a longitudinal center line $A_2$. The transmission member 320 can provide aspiration from and/or irrigation (via the lumen 324, and the connecting lumens of any component to which the transmission member 320 is coupled) to a target tissue site during an ultrasonic procedure.

As shown in FIG. 6, the transmission member 320 includes a proximal end portion 321 and a distal end portion 322. The proximal end portion 321 can be at least operably coupled to an ultrasonic energy source such as the ultrasonic generator 180 and/or the transducer assembly 150 described above. For example, in some embodiments, the proximal end portion 321 can be disposed within a lumen of a coupler, such as coupler 130 described above with reference to FIG. 2, or any of the couplers described in the '775 Publication. In such embodiments, the coupler can be coupled to the ultrasonic energy source 180, thus, operably coupling the transmission member 320 to the ultrasonic energy source 180.

The distal end portion 322 can be disposed within a body to transfer ultrasonic energy from the proximal end portion 321 to a bodily tissue. For example, in some embodiments, the distal end portion can be disposed within a ureter, and can be used to remove a calculus therein, as described below. The distal end portion 322 of the transmission member 320 includes a distal end surface 327 and an engagement surface 325. The distal end surface 327 is devoid of sharp edges and/or is blunt. More particularly, the distal end surface 327 defines a plane that intersects the longitudinal center line $A_2$ at an angle $\theta_2$ of about 90 degrees. In this manner, the likelihood that the distal end surface 327 will perforate, tear or pierce the wall defining the bodily lumen is limited. Although shown as being about 90 degrees, in other embodiments, the distal end surface is between about 75 degrees and about 105 degrees. The distal end surface 327 defines a distal end opening 328 in fluid communication with the lumen 324 of the transmission member 320. The distal end opening 328 can be configured for the aspiration and/or irrigation of a target tissue site via the lumen 324.

The engagement surface 325 of the distal end portion 322 of the transmission member 320 is concave and is configured to engage at least a portion of a target tissue within the bodily lumen to limit movement of the target tissue along the longitudinal center line $A_2$. As a result of being concave, the engagement surface 325 is capable of limiting the movement of a target tissue in both directions along the longitudinal center line $A_2$. In particular, as shown in FIG. 6, the engagement surface 325 is curved and has a first portion 329 and a second portion 330 that is opposite from first portion 329. In use, similarly to the transmission member 220 above, the first portion 329 is configured to engage a first side of a target tissue and the second portion 330 is configured to engage a second side of the target tissue. In this manner, both the distal and proximal movement of the target tissue within a bodily lumen is limited.

In use, a lateral force can be applied to the transmission member 320 to press the engagement surface 325 against the target tissue (e.g., a kidney stone or the like). The lateral force can cause the engagement surface 325 to move the target tissue into contact with a wall defining the bodily lumen (not shown). Continued application of the lateral force can maintain the target tissue in a position between the engagement surface 325 and the wall. The proximal end portion 321 of the transmission member 320 can transmit ultrasonic energy towards the distal end portion 322 such that a portion of the ultrasonic energy is delivered to the target tissue. The target tissue can absorb the ultrasonic energy, causing the target tissue to break into smaller portions. Because the target tissue can be held in place relative to the transmission member 320, the delivery of ultrasonic energy to the target tissue will result in the target tissue breaking apart faster than if the target tissue is freely movable relative to the transmission member 320. Additionally, because the engagement surface 325 can engage the target tissue and hold the target tissue in place relative to the transmission member 320, the amount of movement of the transmission member 320 needed to maintain contact between the transmission member 320 and the target tissue for the delivery of ultrasonic energy will be reduced. The decreased amount of movement of the transmission member 320 reduces the likelihood that the transmission member will damage the wall of the bodily lumen. When the ultrasonic energy has broken the target tissue into portions small enough to be able to move through the lumen 324 of the transmission member 320, the portions of the target tissue can be aspirated through the lumen 324.

The engagement surface 325 defines an opening 326 in fluid communication with the lumen 324. In this manner, portions of the target tissue can be aspirated via the lumen through the opening 326. Moreover, as shown in FIGS. 6 and 7, the engagement surface 325 can be spaced apart from the distal end surface 327. For example, in some embodiments, a length or size of the opening 326 along the longitudinal center line $A_2$ is less than about four times the diameter of the distal end portion 322 of the transmission member 320.

The size and/or shape of the engagement surface 325 is configured to engage, retain and/or surround the target tissue to facilitate the ablation thereof. Although the first portion 329 and the second portion 330 are shown as symmetrical, in other embodiments the first portion 329 and the second portion 330 can be asymmetrical. As a result, the lumen 324 of the transmission member 320 has a reduced likelihood of being obstructed by the target tissue because the target tissue is retained by the engagement surface 325 and the distal end opening 328 remains open. The engagement surface 325 can hold the target tissue in the opening 326 in a position that leaves the distal end opening 328 unobstructed and the lumen 324 at least partially unobstructed along the entire length of the lumen 224. Therefore, the aspiration through the lumen 324 can be maintained when the target tissue is engaged with the engagement surface 325, even if the opening 326 is obstructed or partially obstructed by the target tissue. As the target tissue is broken into smaller portions by the application of ultrasonic energy, the smaller portions can be aspirated through the opening 326 or the distal end opening 328.

In some embodiments, the transmission member can have an engagement surface that intersects the distal end surface. For example, FIGS. 8 and 9 show a transmission member 420 having a distal end surface 427 and an engagement surface 425 intersecting the distal end surface 427. The transmission member 420 can be included in any suitable ultrasonic energy system shown and described herein, such as, for example, the system 100 described above with reference to FIGS. 1 and 2. The transmission member 420 is an elongate member including a side wall 423 and defining a lumen 424 along a longitudinal center line $A_3$. The transmission member 420 can provide aspiration from and/or irrigation (via the lumen 424, and the connecting lumens of any component to which the transmission member 420 is coupled) to a target tissue site during an ultrasonic procedure.

As shown in FIG. 8, transmission member 420 includes a proximal end portion 421 and a distal end portion 422. The proximal end portion 421 can be at least operably coupled to an ultrasonic energy source such as the ultrasonic generator 180 and/or the transducer assembly 150 described above. For example, in some embodiments, the proximal end portion 421 can be disposed within a lumen of a coupler, such as coupler 130 described above with reference to FIG. 2, or any of the couplers described in the '775 Publication. In such embodiments, the coupler can be coupled to the ultrasonic energy source 180, thus, operably coupling the transmission member 420 to the ultrasonic energy source 180.

The distal end portion 422 can be disposed within a body to transfer ultrasonic energy from the proximal end portion 421 to a bodily tissue. For example, in some embodiments, the distal end portion can be disposed within a ureter, and can be used to remove a calculus therein, as described below. The distal end portion 422 of the transmission member 420 includes the distal end surface 427 and the engagement surface 425. The distal end surface 427 is blunt. More particularly, the distal end surface 427 defines a plane that intersects the longitudinal center line $A_3$ at an angle $\theta_3$ of about 90 degrees. In this manner, the likelihood that the distal end surface 427 will perforate, tear or pierce the wall defining the bodily lumen is limited. Although shown as being about 90 degrees, in other embodiments, the distal end surface is between about 75 degrees and about 105 degrees. The distal end surface 427 defines a distal end opening 428 in fluid communication with the lumen 424 of the transmission member 424. The distal end opening 428 can be configured for the aspiration and/or irrigation of a target tissue site via the lumen 424.

The engagement surface 425 of the distal end portion 422 of the transmission member 420 is concave and is configured to engage at least a portion of a target tissue within the bodily lumen to limit movement of the target tissue along the longitudinal center line $A_3$. As a result of being concave, the engagement surface 425 is capable of limiting the movement of a target tissue in both directions along the longitudinal center line $A_3$. In particular, as shown in FIG. 8, the engagement surface 425 is curved and has a first portion 429 and a second portion 430 that is opposite from first portion 429. In use, the first portion 429 is configured to engage a first side of a target tissue and the second portion 430 is configured to engage a second side of the target tissue. In this manner, both the distal and proximal movement of the target tissue within a bodily lumen is limited.

The engagement surface 425 intersects the distal end surface 427 and defines an opening 426 in fluid communication with the lumen 424. In this manner, the distal end opening 428 and the opening 426 are contiguous and/or share a common boundary. Similarly stated, the distal end opening 428 and the opening 426 in the engagement surface 425 intersect so that the lumen 424 of the transmission member 420 is accessible from the distal end opening 428 to the first portion 429. Although the intersection between the engagement surface 425 and the distal end surface 427 is shown as being sharp, in other embodiments, the intersection can include a chamfer, edge break or other feature to limit the likelihood that the intersection will damage, perforate or tear the wall of a bodily lumen.

The size and/or shape of the engagement surface 425 is configured to engage, retain and/or surround the target tissue to facilitate the ablation thereof. In some embodiments, a distance between the first portion 429 and the second portion 430 is less than about four times a diameter of the distal end portion 422 of the transmission member 420. In some embodiments, a length or size of the opening 426 along the longitudinal center line $A_3$ is less than about four times the diameter of the distal end portion 422 of the transmission member 420. As a result, the engagement surface 425 can hold the target tissue in the opening 426 in a position that leaves the distal end opening 428 unobstructed and the lumen 424 at least partially unobstructed along the entire length of the lumen 224. Therefore, the aspiration through the lumen 424 can be maintained when the target tissue is engaged with the engagement surface 425, even if the opening 426 is obstructed or partially obstructed by the target tissue. As the target tissue is broken into smaller portions by the application of ultrasonic energy, the smaller portions can be aspirated through the enlarged opening formed by opening 426 and the distal end opening 428.

As described above, in use, a lateral force can be applied to the transmission member 420 to press the engagement surface 425 against the target tissue (e.g., a kidney stone or the like). The lateral force can cause the engagement surface 425 to move the target tissue into contact with a wall defining the bodily lumen (not shown). Continued application of the lateral force can maintain the target tissue in a position between the engagement surface 425 and the wall. The proximal end portion 421 of the transmission member 420 can transmit ultrasonic energy towards the distal end portion 422 such that a portion of the ultrasonic energy is delivered to the target tissue. The target tissue can absorb the ultrasonic energy, causing the target tissue to break into smaller portions. Because the target tissue can be held in place relative to the transmission member 420, the delivery of ultrasonic energy to the target tissue will result in the target tissue breaking apart faster than if the target tissue is freely movable relative to the transmission member 420. Additionally, because the engagement surface 425 can engage the target tissue and hold the target tissue in place relative to the transmission member 420, the amount of movement of the transmission member 420 needed to maintain contact between the transmission member 420 and the target tissue for the delivery of ultrasonic energy will be reduced. The decreased amount of movement of the transmission member 420 reduces the likelihood that the transmission member 420 will damage the wall of the bodily lumen. When the ultrasonic energy has broken the target tissue into portions small enough to be able to move through the lumen 424 of the transmission member 420, the portions of the target tissue can be aspirated through the lumen 424.

Figure 10:
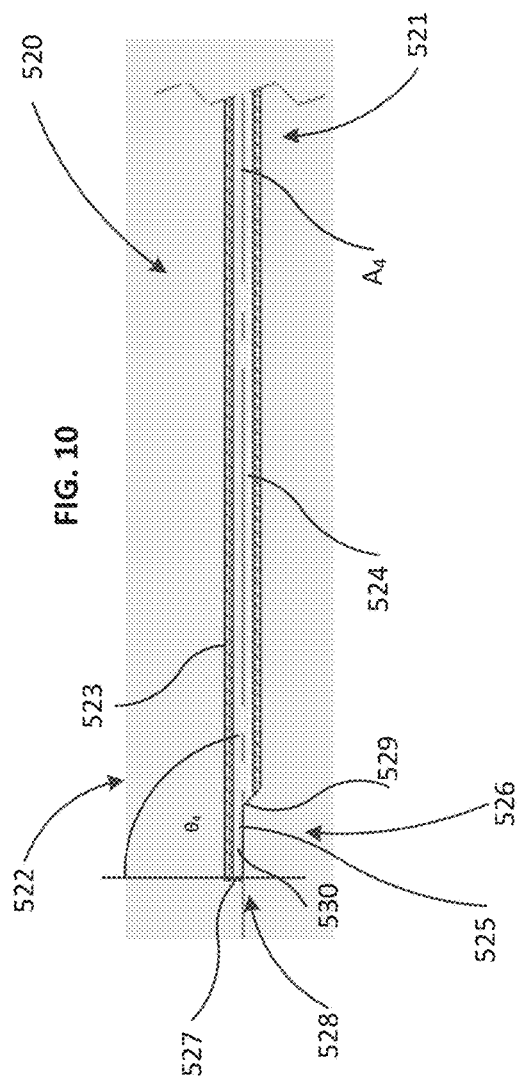
FIG. 10 is a cross-sectional side view of a transmission member, according to an embodiment.
Figure 11:
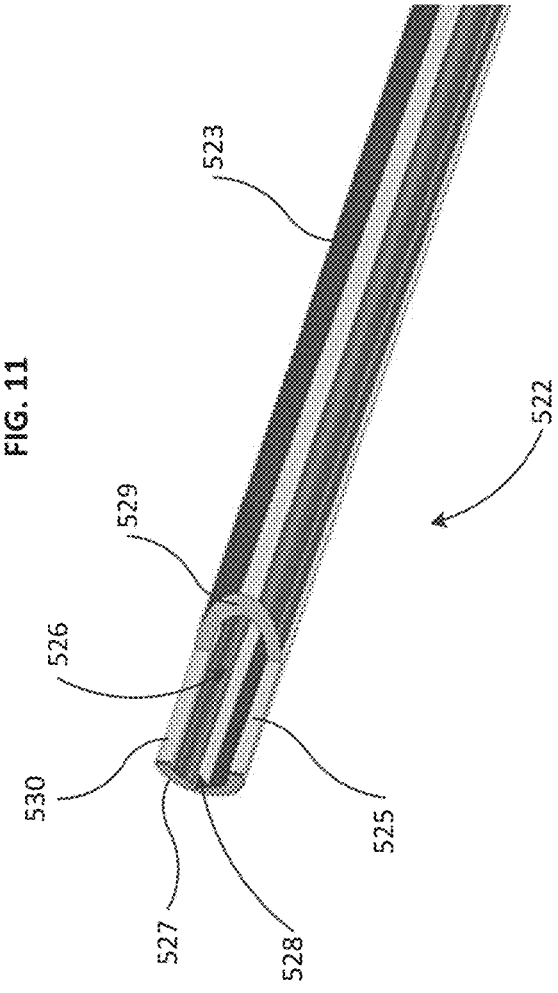
FIG. 11 is a side perspective view of the transmission member shown in FIG. 10.

As shown in FIGS. 8 and 9, the engagement surface 425 can be substantially continuous. In other embodiments, the engagement surface can include intersecting discontinuous edges, such as the engagement surface 225 described above. As another example, FIGS. 10 and 11 show a transmission member 520 having a discontinuous engagement surface 525, a portion of which intersects the distal end surface 527. The transmission member 520 can be included in any suitable ultrasonic energy system shown and described herein, such as, for example, the system 100 described above with reference to FIGS. 1 and 2. The transmission member 520 is an elongate member including a side wall 523 and defining a lumen 524 along a longitudinal center line $A_4$. The transmission member 520 can provide aspiration from and/or irrigation (via the lumen 524, and the connecting lumens of any component to which the transmission member 520 is coupled) to a target tissue site during an ultrasonic procedure.

As shown in FIG. 10, transmission member 520 includes a proximal end portion 521 and a distal end portion 522. The proximal end portion 521 can be at least operably coupled to an ultrasonic energy source such as the ultrasonic generator 180 and/or the transducer assembly 150 described above. For example, in some embodiments, the proximal end portion 521 can be disposed within a lumen of a coupler, such as coupler 130 described above with reference to FIG. 2, or any of the couplers described in the '775 Publication. In such embodiments, the coupler can be coupled to the ultrasonic energy source 180, thus, operably coupling the transmission member 520 to the ultrasonic energy source 180.

The distal end portion 522 can be disposed within a body to transfer ultrasonic energy from the proximal end portion 521 to a bodily tissue. For example, in some embodiments, the distal end portion can be disposed within a ureter, and can be used to remove a calculus therein, as described below. The distal end portion 522 of the transmission member 520 includes the distal end surface 527 and the engagement surface 525. The distal end surface 527 is blunt. More particularly, the distal end surface 527 defines a plane that intersects the longitudinal center line $A_4$ at an angle $\theta_4$ of about 90 degrees. In this manner, the likelihood that the distal end surface 527 will perforate, tear or pierce the wall defining the bodily lumen is limited. Although shown as being about 90 degrees, in other embodiments, the distal end surface is between about 75 degrees and about 105 degrees. The distal end surface 527 defines a distal end opening 528 in fluid communication with the lumen 524 of the transmission member 524. The distal end opening 528 can be configured for the aspiration and/or irrigation of a target tissue site via the lumen 524.

The engagement surface 525 of the distal end portion 522 of the transmission member 520 is concave and is configured to engage at least a portion of a target tissue within the bodily lumen to limit movement of the target tissue along the longitudinal center line $A_4$. As a result of being concave, the engagement surface 525 is capable of limiting the movement of a target tissue in the proximal direction along the longitudinal center line $A_4$. In particular, as shown in FIG. 10, the engagement surface 525 has a first portion 529 and a second portion 530 that intersect to form a discontinuous surface. In use, the first portion 529 is configured to engage a first side of a target tissue and the second portion 530 is configured to engage a second side of the target tissue. In this manner, the proximal movement of the target tissue within a bodily lumen is limited by the second portion 529.

In use, a lateral force can be applied to the transmission member 520 to press the engagement surface 525 against the target tissue (e.g., a kidney stone or the like). The lateral force can cause the engagement surface 525 to move the target tissue into contact with a wall defining the bodily lumen (not shown). Continued application of the lateral force can maintain the target tissue in a position between the engagement surface 525 and the wall. The proximal end portion 521 of the transmission member 520 can transmit ultrasonic energy towards the distal end portion 522 such that a portion of the ultrasonic energy is delivered to the target tissue. The target tissue can absorb the ultrasonic energy, causing the target tissue to break into smaller portions. Because the target tissue can be held in place relative to the transmission member 520, the delivery of ultrasonic energy to the target tissue will result in the target tissue breaking apart faster than if the target tissue is freely movable relative to the transmission member 520. Additionally, because the engagement surface 525 can engage the target tissue and hold the target tissue in place relative to the transmission member 520, the amount of movement of the transmission member 520 needed to maintain contact between the transmission member 520 and the target tissue for the delivery of ultrasonic energy will be reduced. The decreased amount of movement of the transmission member 520 reduces the likelihood that the transmission member 520 will damage the wall of the bodily lumen. When the ultrasonic energy has broken the target tissue into portions small enough to be able to move through the lumen 524 of the transmission member 520, the portions of the target tissue can be aspirated through the lumen 524.

The engagement surface 525 intersects the distal end surface 527 and defines an opening 526 in fluid communication with the lumen 524. In this manner, the distal end opening 528 and the opening 526 are contiguous and/or share a common boundary. Similarly stated, the distal end opening 528 and the opening 526 in the engagement surface 525 intersect so that the lumen 524 of the transmission member 520 is accessible from the distal end opening 528 to the first portion 529. Although the intersection between the second portion 530 of the engagement surface 525 and the distal end surface 527 is shown as being sharp, in other embodiments, the intersection can include a chamfer, edge break or other feature to limit the likelihood that the intersection will damage, perforate or tear the wall of a bodily lumen.

The size and/or shape of the engagement surface 525 is configured to engage, retain and/or partially surround the target tissue to facilitate the ablation thereof. In some embodiments, a length of the opening 526 along the longitudinal center line $A_4$ is less than about four times the diameter of the distal end portion 522 of the transmission member 520. In other embodiments, the second portion 530 of the engagement surface 525 can be nonparallel to the longitudinal center line $A_4$.

In some embodiments, rather than having a concave or partially concave surface, a transmission member can have a substantially flat engagement surface. For example, FIGS. 12 and 13 show a transmission member 620 having a substantially flat engagement surface 625. The transmission member 620 can be included in any suitable ultrasonic energy system shown and described herein, such as, for example, the system 100 described above with reference to FIGS. 1 and 2. The transmission member 620 is an elongate member including a side wall 623 and defining a lumen 624 along a longitudinal center line $A_5$. The transmission member 620 can provide aspiration from and/or irrigation (via the lumen 624, and the connecting lumens of any component to which the transmission member 620 is coupled) to a target tissue site during an ultrasonic procedure.

As shown in FIG. 12, the transmission member 620 includes a proximal end portion 621 and a distal end portion 622. The proximal end portion 621 can be at least operably coupled to an ultrasonic energy source such as the ultrasonic generator 180 and/or the transducer assembly 150 described above. For example, in some embodiments, the proximal end portion 621 can be disposed within a lumen of a coupler, such as coupler 130 described above with reference to FIG. 2, or any of the couplers described in the '775 Publication. In such embodiments, the coupler can be coupled to the ultrasonic energy source 180, thus, operably coupling the transmission member 620 to the ultrasonic energy source 180.

The distal end portion 622 can be disposed within a body to transfer ultrasonic energy from the proximal end portion 621 to a bodily tissue. For example, in some embodiments, the distal end portion can be disposed within a ureter, and can be used to remove a calculus therein, as described below. The distal end portion 622 of the transmission member 620 includes the distal end surface 627 and the engagement surface 625. The distal end surface 627 is blunt. More particularly, the distal end surface 627 defines a plane that intersects the longitudinal center line $A_5$ at an angle $\theta_5$ of about 90 degrees. In this manner, the likelihood that the distal end surface 627 will perforate, tear or pierce the wall defining the bodily lumen is limited. Although shown as being about 90 degrees, in other embodiments, the distal end surface is between about 75 degrees and about 105 degrees. The distal end surface 627 defines a distal end opening 628 in fluid communication with the lumen 624 of the transmission member 624. The distal end opening 628 can be configured for the aspiration and/or irrigation of a target tissue site via the lumen 624.

The engagement surface 625 of the distal end portion 622 of the transmission member 620 is substantially flat (or planar) and is configured to engage at least a portion of a target tissue within the bodily lumen to limit movement of the target tissue proximally along the longitudinal center line $A_5$. Additionally, when the transmission member 620 is moved distally within the bodily lumen, the engagement surface 625 is also capable of moving the target tissue distally along the longitudinal center line $A_5$.

In use, a lateral force can be applied to the transmission member 620 to press the engagement surface 625 against the target tissue (e.g., a kidney stone or the like). The lateral force can cause the engagement surface 625 to move the target tissue into contact with a wall defining the bodily lumen (not shown). Continued application of the lateral force can maintain the target tissue in a position between the engagement surface 625 and the wall. The proximal end portion 621 of the transmission member 620 can transmit ultrasonic energy towards the distal end portion 622 such that a portion of the ultrasonic energy is delivered to the target tissue. The target tissue can absorb the ultrasonic energy, causing the target tissue to break into smaller portions. Because the target tissue can be held in place relative to the transmission member 620, the delivery of ultrasonic energy to the target tissue will result in the target tissue breaking apart faster than if the target tissue is freely movable relative to the transmission member 620. Additionally, because the engagement surface 625 can engage the target tissue and hold the target tissue in place relative to the transmission member 620, the amount of movement of the transmission member 620 needed to maintain contact between the transmission member 620 and the target tissue for the delivery of ultrasonic energy will be reduced. The decreased amount of movement of the transmission member 620 reduces the likelihood that the transmission member 620 will damage the wall of the bodily lumen. When the ultrasonic energy has broken the target tissue into portions small enough to be able to move through the lumen 624 of the transmission member 620, the portions of the target tissue can be aspirated through the lumen 624.

The engagement surface 625 intersects the distal end surface 627 and defines an opening 626 in fluid communication with the lumen 624. In this manner, the distal end opening 628 and the opening 626 are contiguous and/or share a common boundary. Although the intersection between the second portion 630 of the engagement surface 625 and the distal end surface 627 is shown as being sharp, in other embodiments, the intersection can include a chamfer, edge break or other feature to limit the likelihood that the intersection will damage, perforate or tear the wall of a bodily lumen.

The size and/or shape of the engagement surface 625 is configured to engage, retain and/or partially surround the target tissue to facilitate the ablation thereof. In some embodiments, a length of the engagement surface 625 is less than about four times a diameter of the distal end portion 622 of the transmission member 620. In some embodiments, a length of the opening 626 along the longitudinal center line $A_5$ is less than about four times the diameter of the distal end portion 622 of the transmission member 620.

Figure 14:
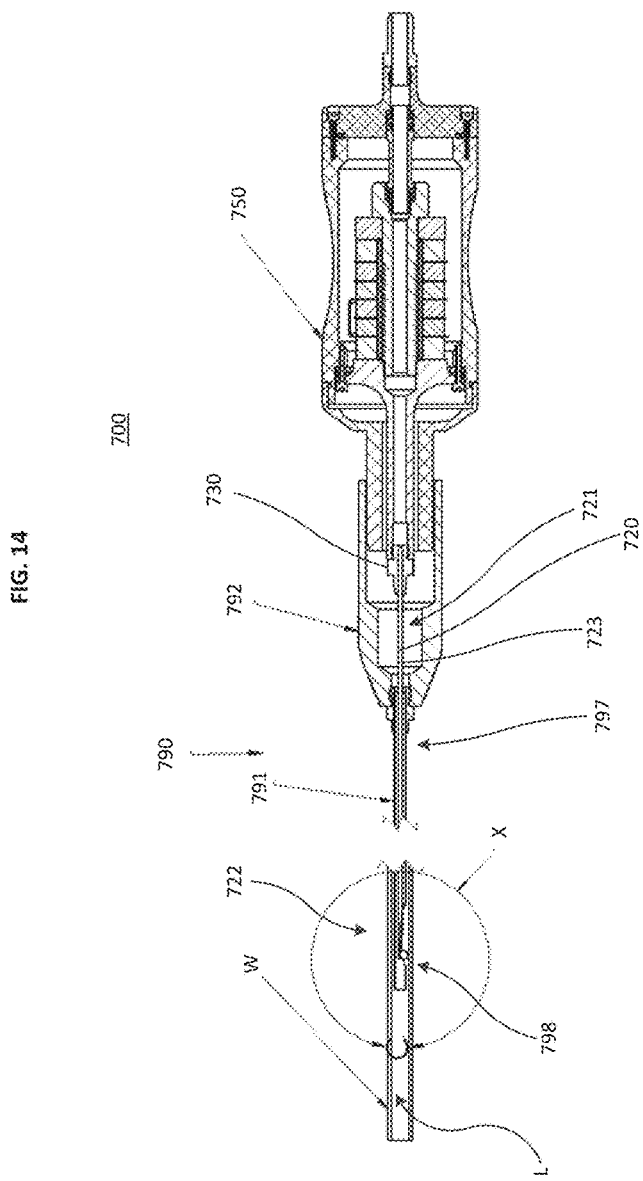
FIG. 14 is a cross-sectional side view of an ablation assembly, according to an embodiment.

Although the transmission members are shown and described above as monolithic structures that include a surface being shaped or sized to engage a target tissue and/or limit migration of the target tissue within a bodily lumen, in other embodiments a transmission member or assembly can include multiple components that cooperatively function to engage and/or limit movement of a target tissue. For example, FIG. 14 is a cross sectional view of an ablation assembly 700 according to an embodiment. The ablation assembly 700 can be included in any suitable ultrasonic energy system shown and described herein, such as, for example, the system 100 described above with reference to FIGS. 1 and 2. The ablation assembly 700 includes an ultrasonic transducer assembly 750, a sheath assembly 790, and a transmission member 720. The ultrasonic transducer assembly 750 is similar to ultrasonic transducer assembly 150 described above, and will not be further described herein. The sheath assembly 790 includes a sheath 791 and a sheath base 792. The sheath 791 is configured to be inserted into a bodily lumen L. The bodily lumen L can be a ureter. In some embodiments, the sheath base 792 is removably coupled to the transducer assembly 750. For example, the sheath base can be removably coupled to the transducer assembly via a friction fit, a threaded coupling, or any other suitable method.

Figure 15:
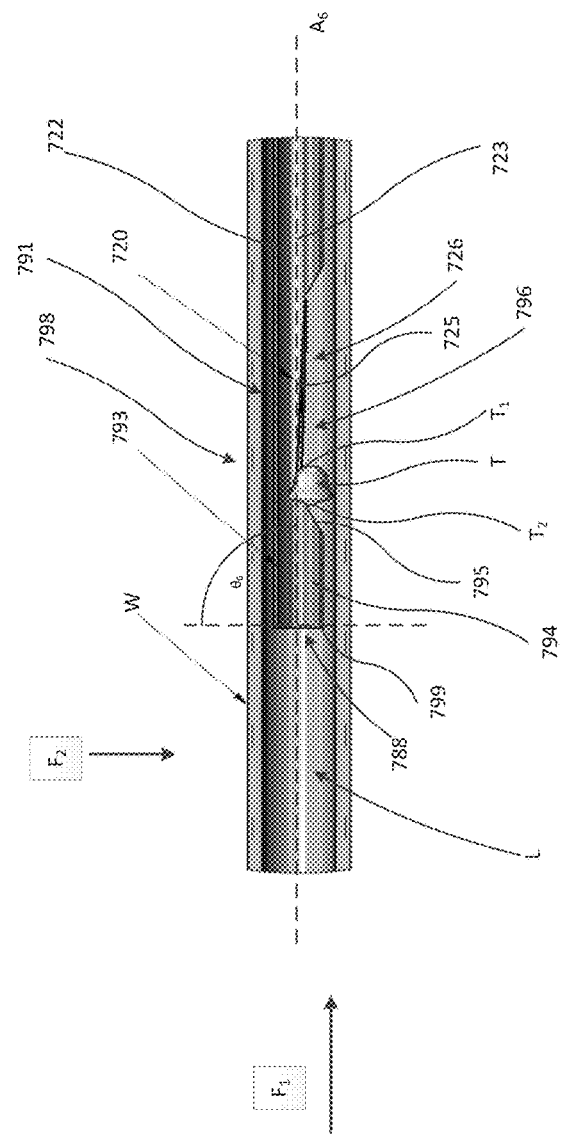
FIG. 15 is an enlarged view of the portion of the transmission member of FIG. 14 shown in the region marked X.

As shown in FIG. 14 and in FIG. 15, which is an enlarged view of the portion of the ablation assembly 700 of FIG. 14 shown in the region identified as region X, the transmission member 720 is an elongate member including a side wall 723 and defining a lumen (not shown) along a longitudinal center line $A_6$. The transmission member 720 can provide aspiration from and/or irrigation (via the lumen, and the connecting lumens of any component to which the transmission member 720 is coupled) to a target tissue (e.g., a calculus) during an ultrasonic procedure. The transmission member 720 includes a proximal end portion 721 and a distal end portion 722. The proximal end portion 721 can be at least operably coupled to an ultrasonic energy source such as the ultrasonic generator 180 and/or the transducer assembly 750. For example, in some embodiments, the proximal end portion 721 can be disposed within a lumen of a coupler 730. The coupler 730 can be similar to the coupler 130 described above with reference to FIGS. 2 and 18, or any of the couplers described in the '775 Publication. In such embodiments, the coupler can be coupled to the ultrasonic energy source 180, thus, operably coupling the transmission member 720 to the ultrasonic energy source 180.

As shown in FIG. 15, the distal end portion 722 of the transmission member 720 and the sheath 791 are configured to be inserted into a bodily lumen L. The transmission member 722 is configured to transfer ultrasonic energy from the proximal end portion 721 to the distal end portion 722 and to a bodily tissue T. For example, in some embodiments, the distal end portion can be disposed within a ureter, and can be used to remove a calculus therein, as described below. As shown in FIG. 15, the distal end portion 722 of the transmission member 720 includes a first engagement surface 725. The first engagement surface defines an opening 726 in fluid communication with the lumen (not shown) of the transmission member 720.

The sheath 791 is an elongate member including a side wall 793 and defining a lumen 794 along the longitudinal center line $A_6$. The sheath 791 includes a proximal end portion 797 and a distal end portion 798. The proximal end portion 797 is coupled to the sheath base 792 by any suitable method. In this manner, movement of the sheath base 792 produces movement of the sheath 791. For example, the proximal end portion 797 can be coupled to the sheath base by a mechanical fastener, welding, an adhesive bond or the like. In some embodiments, the sheath 791 and the sheath base 792 can be monolithically constructed.

The sheath 791 is configured to be movably disposed about at least the distal end portion 722 of the transmission member 720. The distal end portion 798 of the sheath 791 can extend beyond the distal end portion 722 of the transmission member 720, thereby deterring the distal end portion 722 of the transmission member 720 from puncturing a wall W of the bodily lumen L. Specifically, the distal end portion 798 of the sheath 791 can include a distal end surface 799. The distal end surface 799 of the sheath 791 can be devoid of sharp edges and/or can be blunt. More particularly, the distal end surface 799 of the sheath 791 defines a plane that intersects the longitudinal center line $A_6$ at an angle $\theta_6$ of about 90 degrees. In this manner, the likelihood that the distal end surface 799 will perforate, tear or pierce the wall W defining the bodily lumen L is limited. Although shown as being about 90 degrees, in other embodiments, the distal end surface 799 is between about 75 degrees and about 105 degrees. The distal end surface 799 of the sheath 791 defines a distal end opening 788 in fluid communication with the lumen 794 of the sheath 791.

The distal end portion 798 of the sheath 791 also includes a second engagement surface 795. The second engagement surface 795 can define at least a portion of a sheath opening 796. The first engagement surface 725 of the transmission member 720 and the second engagement surface 795 of the sheath 791 are configured to engage a target tissue T within the bodily lumen L to cooperatively limit movement of the target tissue along the longitudinal center line $A_6$. The sheath 791 can be moved into a position within a bodily lumen L such that the second engagement surface 795 engages with a second side $T_2$ of the target tissue T. After the sheath 791 is in position, the transmission member 720 can be moved distally within the lumen 794 of the sheath 791 such that the first engagement surface 725 of the transmission member 720 engages with a first side $T_1$ of the target tissue T. The first engagement surface 725 of the transmission member 720 and the second engagement surface 795 of the sheath 791 can collectively form a concave surface configured to surround at least a portion of the target tissue T. In this manner, the location of the target tissue T relative to the bodily lumen L can be controlled between the first engagement surface 725 and the second engagement surface 795. The proximal movement of the target tissue T within the bodily lumen is limited by the first engagement surface 725 and the distal movement of the target tissue T within a bodily lumen is limited by the second engagement surface 795.

Thus, the first engagement surface 725 (of the transmission member 720) and the second engagement surface 795 (of the sheath 791) are configured to engage, retain and/or surround the target tissue T to facilitate the ablation thereof. For example, as shown in FIG. 15, the slope of the first engagement surface 725 can be negative and the slope of the second engagement surface 795 can be positive. In this manner, the shape of the engagement surfaces can prevent both distal (or backward) migration of the target tissue T (i.e., by engagement with the positive-sloped second engagement surface 795) and proximal (or forward) migration of the target tissue T (i.e., by engagement with the negative-sloped first engagement surface 725). Although shown as asymmetrical about an axis normal to the longitudinal center line $A_6$), in other embodiments the slope of the first engagement surface 725 and the slope of the second engagement surface 795 can be parallel or symmetrical about such an axis.

Moreover, because the sheath 791 can move relative to the transmission member 720, a proximal force along the longitudinal center line $A_6$ can be applied to the sheath (as shown by the arrow $F_1$). When the force $F_1$ is applied, the second engagement surface 795 can press and/or pinch the target tissue T against the first engagement surface 725. In this manner, the first engagement surface 725 (of the transmission member 720) and the second engagement surface 795 (of the sheath 791) are configured to actively engage, retain and/or surround the target tissue T to facilitate the ablation thereof.

In addition to the axial force $F_1$, a lateral force (as shown by the arrow $F_2$) can be applied to the transmission member 720 and/or the sheath 791 to press the first engagement surface 725 and/or the second engagement surface 795 against the target tissue T. The lateral force $F_2$ can cause the first engagement surface 725 and/or the second engagement surface 795 to move the target tissue T into contact with the wall W defining the bodily lumen L. Continued application of the lateral force can maintain the target tissue T in a position between the first engagement surface 725, the second engagement surface 795, and the wall W. The proximal end portion 721 of the transmission member 720 can transmit ultrasonic energy towards the distal end portion 722 such that a portion of the ultrasonic energy is delivered to the target tissue T. The target tissue T can absorb the ultrasonic energy, causing the target tissue T to break into smaller portions. Because the target tissue T can be held in place relative to the transmission member 720 by the first engagement surface 725 and the second engagement surface 795, the delivery of ultrasonic energy to the target tissue T will result in the target tissue T breaking apart faster than if the target tissue T is freely movable relative to the transmission member 720. Additionally, because the first engagement surface 725 and the second engagement surface 795 can collectively engage the target tissue T and hold the target tissue T in place relative to the transmission member 720, the amount of movement of the transmission member 720 and the sheath 791 needed to maintain contact between the transmission member 720 and the target tissue T for the delivery of ultrasonic energy will be reduced. The decreased amount of movement of the transmission member 720 and the sheath 791 reduces the likelihood that the transmission member 720 or the sheath 791 will damage the wall W of the bodily lumen L. The sheath opening 796 can be configured to be aligned with the opening 726 of the transmission member 720. When the ultrasonic energy has broken the target tissue T into portions small enough to be able to move through the lumen of the transmission member 720, the portions of the target tissue T can be aspirated through the sheath opening 796, through the opening 726 of the transmission member 720, and then through the lumen of the transmission member 720.

Although the distal end portion 722 of the transmission member 720 is shown as including a sharp tip, in other embodiments, the distal end portion 722 of the transmission member 720 can include a distal end surface (similar to that shown in the transmission members 420, 520, and 620 of FIGS. 8-13). In such embodiments, the first engagement surface 725 can intersect the distal end surface. The second engagement surface 795 can be disposed distally from the distal end surface of the transmission member 720. In this manner, the distal end surface and/or the first engagement surface 725 can engage a first side of the target tissue T and the second engagement surface 795 of the sheath 791 can engage a second side of the target tissue T.

Although the transmission member 720 is shown as having a flat engagement surface in FIGS. 14 and 15, the sheath can be used with any of the transmission members described herein. Additionally, although the sheath 791 is shown as having a concave engagement surface with intersecting discontinuous edges, the engagement surface of the sheath 791 can include the shape of any of the engagement surfaces of any of the devices described herein.

FIG. 16 is a flow chart of a method 800 according to an embodiment. The method 800 includes inserting at least a distal end portion of a transmission member into a bodily lumen, at 802. The transmission member, which can be any of the transmission members shown and described herein, defines a lumen along a longitudinal center line of the transmission member. The distal end portion of the transmission member includes a concave engagement surface defining an opening in fluid communication with the lumen. In some embodiments, the concave engagement surface can be substantially continuous or can have intersecting discontinuous edges. In some embodiments, the distal end portion of the transmission member can include a distal end surface defining a plane that intersects the longitudinal center line at an angle of between about 75 degrees and about 105 degrees. The distal end surface can be maintained at a location outside of the target tissue during insertion of at least the distal end portion of the transmission member into the bodily lumen.

A target tissue is contacted within the bodily lumen is contacted with the concave engagement surface of the transmission member to limit movement of the target tissue along the longitudinal center line, at 804. In some embodiments, the bodily lumen can be a ureter and the target tissue can be a calculus. The distal end surface can be maintained at a location outside of the target tissue when the target tissue is contacted with the concave engagement surface of the transmission member. At least a portion of the target tissue can be surrounded with the concave engagement surface. In some embodiments, a lateral force can be exerted against a first portion of the target tissue via the engagement surface such that a second portion of the target tissue is maintained in contact with a wall defining the bodily lumen.

Ultrasonic energy is then transmitted from a proximal end portion of the transmission member towards the distal end portion such that a portion of the ultrasonic energy is delivered to the target tissue within the bodily lumen, at 806. For example, in some embodiments, the proximal end portion of the transmission member can be operably coupled to an ultrasonic energy source such that the ultrasonic energy source supplies the ultrasonic energy to the transmission member.

The method 800 can include aspirating at least a portion of the target tissue via the lumen defined by the transmission member. A negative pressure can be applied to the proximal end portion of the transmission member such that a portion of the target tissue (e.g., a portion of the target tissue that is broken apart by ultrasonic energy) can be aspirated through the lumen defined by the transmission member.

In some embodiments, a sheath, such as the sheath assembly 790 or any other suitable sheath, can be moved relative to the transmission member. The sheath can be disposed about at least the distal end portion of the transmission member to engage the target tissue with an engagement surface of the sheath. The engagement surface of the transmission member and the engagement surface of the sheath can collectively form a concave surface to engage the target tissue and maintain the position of the target tissue during the transmission of ultrasonic energy.

Figure 17:
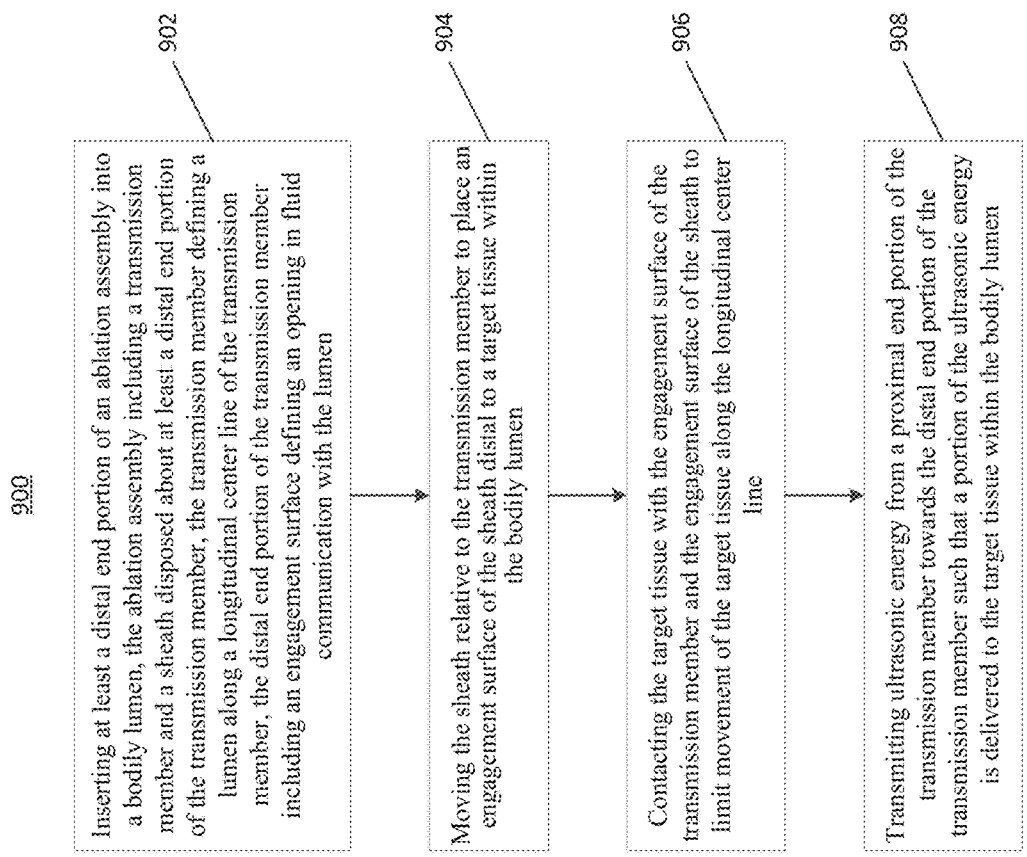
FIG. 17 is a flow chart of a method, according to an embodiment.

FIG. 17 is a flow chart of a method 900 according to an embodiment. The method 900 includes inserting at least a distal end portion of an ablation assembly into a bodily lumen, at 902. The ablation assembly includes a transmission member and a sheath disposed about at least a distal end portion of the transmission member. In some embodiments, the ablation assembly can include the assembly 700 shown and described above. The transmission member defines a lumen along a longitudinal center line of the transmission member. The distal end portion of the transmission member includes an engagement surface defining an opening in fluid communication with the lumen.

The sheath is moved relative to the transmission member to place an engagement surface of the sheath distal to a target tissue within the bodily lumen, at 904. Next, the target tissue is contacted with the engagement surface of the transmission member and the engagement surface of the sheath to limit movement of the target tissue along the longitudinal center line, at 906. Ultrasonic energy is transmitted from a proximal end portion of the transmission member towards the distal end portion of the transmission member such that a portion of the ultrasonic energy is delivered to the target tissue within the bodily lumen, at 908. The bodily lumen can be a ureter and the target tissue can be a calculus, and the method 900 can include aspirating at least a portion of the calculus via the lumen defined by the transmission member.

The transmission members described herein can be monolithically constructed or can be constructed from two or more separately constructed components that are later joined together. The transmission members described herein can be made of any suitable material, such as, for example Type 304 stainless steel, Type 316 stainless steel, nickel titanium alloy (nitinol), or any other super elastic metal or metal alloy. The sheaths described herein can also be made of any suitable material, such as, for example Type 304 stainless steel, Type 316 stainless steel, nickel titanium alloy (nitinol), or any other super elastic metal or metal alloy. In some embodiments, a sheath can be shaped and constructed of material, such as stainless steel, so that the sheath is capable of reflecting ultrasonic energy emitted from a transmission member toward a target tissue.

The embodiments and/or components described herein can be packaged independently or any portion of the embodiments can be packaged together as a kit. For example, in some embodiments, a kit can include an ultrasonic transducer assembly (e.g., such as the ultrasonic transducer assembly 150 described above with reference to FIG. 2) and any suitable number of transmission members (e.g., such as the various embodiments described above with reference to FIGS. 3-15). The transmission members included in the kit can each define a given engagement surface that can be different from the engagement surfaces of the other transmission members included in the kit. For example, in some embodiments, each of the transmission members included in the kit can be substantially similar in size and shape as the other transmission members included in the kit but each transmission member can each define an engagement surface that is substantially unique to the specific transmission member. In this manner, one or more transmission members can define an engagement surface of unique shape, size, or configuration.

In some embodiments, a kit can include an ultrasonic generator similar to the ultrasonic generator 180 shown and described above. The processor included in any of the ultrasonic generators can be a general purpose processor (e.g., a central processing unit (CPU)) or other processor configured to execute one or more instructions stored in the memory. In some embodiments, the processor can alternatively be an application-specific integrated circuit (ASIC) or a field programmable gate array (FPGA). The processor can be configured to execute specific modules and/or submodules that can be, for example, hardware modules, software modules stored in the memory and executed in the processor, and/or any combination thereof. The memory included in the ultrasonic generator 180 can be, for example, flash memory, one time programmable memory, a random access memory (RAM), a memory buffer, a hard drive, a read-only memory (ROM), an erasable programmable read-only memory (EPROM), and/or so forth. In some embodiments, the memory includes a set of instructions to cause the processor to execute modules, processes and/or functions used to generate, control, amplify, and/or transfer electric current to another portion of the system, for example, the transducer assembly 150.

Figure 18:
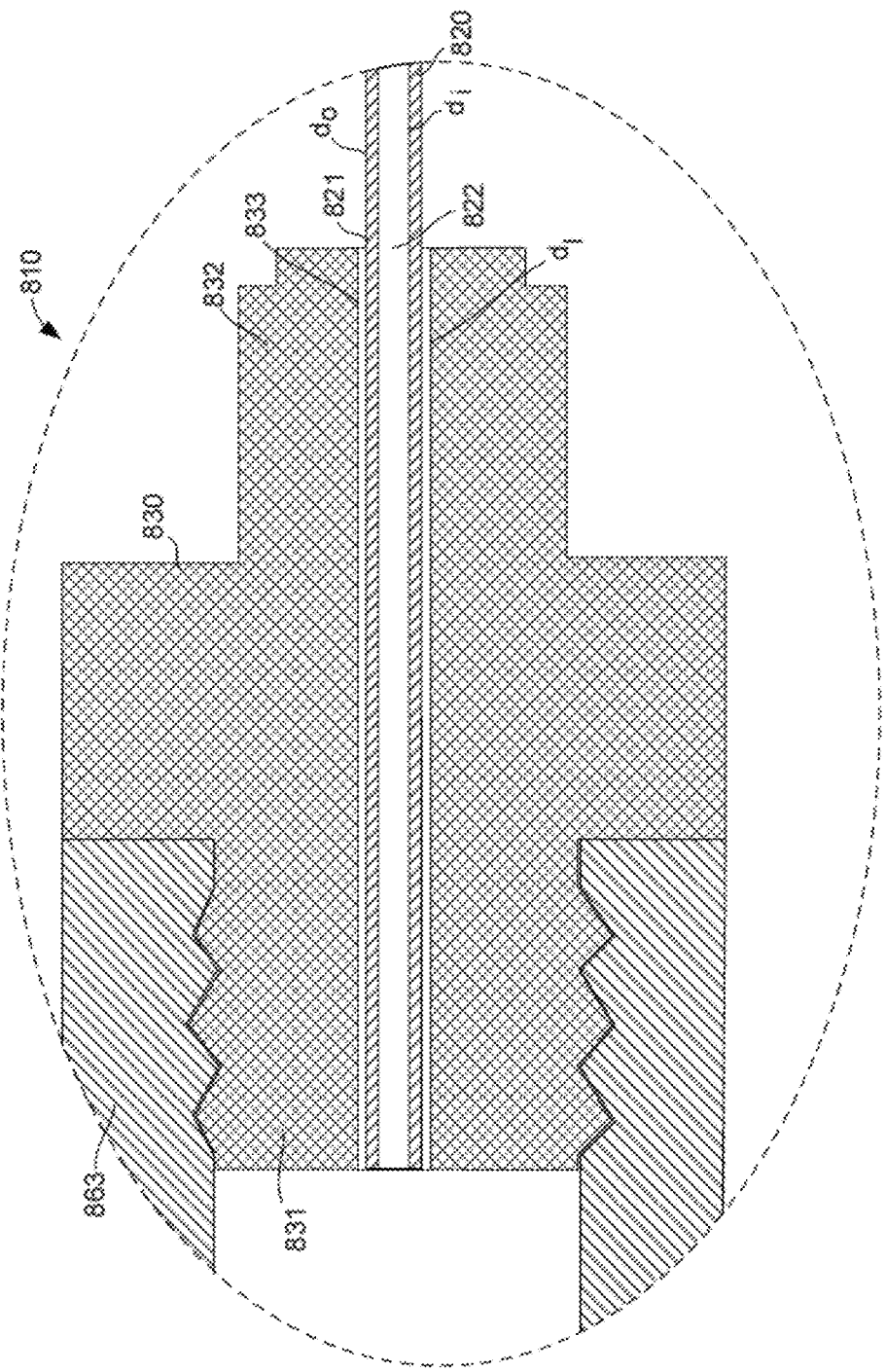
FIG. 18 is an enlarged view of a portion of a probe assembly according to an embodiment coupled to a transducer horn.

The ultrasonic transmission members described herein can be fabricated and/or produced using any suitable methods. In some embodiments a transmission member can be formed via one of more manufacturing process. For example, in some embodiments, a transmission member can be formed via a tube drawing (e.g., drawn through a progressively smaller die (an extrusion process). In embodiments wherein the transmission member defines an engagement surface defining an opening (e.g., the transmission member 220 described above), the opening can be formed via water jet cutting, laser cutting, machining (e.g., milling, turning, shearing, etc.). The proximal end portion of any of the transmission members described herein can be coupled to the coupler member (e.g., the coupler member 130 or the coupler member 730) using any suitable mechanism. For example, as shown in FIG. 18, a probe assembly 810 can include at least a transmission member 820 and a coupler 830. The transmission member 820 and the coupler 830 can be substantially similar to the transmission member 120 and the coupler 130 described above with reference to FIGS. 1 and 2, thus, some portions of the transmission member 820 and the coupler 830 are not described in further detail herein. As shown, the coupler 830 includes a proximal end portion 831 and a distal end portion 832 and defines a lumen 833 therethrough. The proximal end portion 831 is configured to form a threaded coupling with a transducer horn 863, as described above in detail with reference to FIG. 2. The lumen 833 has a diameter $d_l$ that can be any suitable size. In this manner, the coupler 830 can be configured to receive (within the lumen 833) a portion of the transmission member 820, as described in further detail herein.

The transmission member 820 includes a proximal end portion 821 and a distal end portion (not shown in FIG. 18) and defines a lumen 822 therethrough. The transmission member 820 can be any suitable shape, size, or configuration. For example, in some embodiments, at least a portion of the transmission member 820 is substantially annular and includes an outer diameter $d_o$ and an inner diameter $d_i$. In some embodiments, the size and shape of the transmission member 820 (e.g., the outer diameter $d_o$) can substantially correspond to the size and shape (e.g., the diameter $d_l$) of the lumen 833 defined by the coupler 830 such that the proximal end portion 821 of the transmission member 820 can be disposed therein.

For example, in some embodiments, the diameter $d_l$ of the lumen 833 can be greater than the outer diameter $d_o$ of the transmission member 830, thus, the transmission member 820 can be disposed within the lumen 833 of the coupler 830. Furthermore, with the diameter $d_l$ of the lumen 833 greater than the outer diameter $d_o$ of the transmission member 820 an adhesive can be disposed within a void between the transmission member 820 and the inner surface of the coupler 830. Thus, the transmission member 820 can be fixedly coupled to the coupler 830 without the need for crimping, applying a compressive force to the transmission member or the like. Expanding further, the transmission member 820 can be fixedly coupled to the coupler 830 without plastically (e.g., permanently) deforming the transmission member, thereby decreasing the likelihood of failure and also decreasing losses due to reflections of ultrasonic energy produced by discontinuity. In other embodiments, the transmission member 120 can be coupled via welding or brazing while still realizing the benefits described above.

The transmission members described herein can be any suitable size. For example, in some embodiments, a transmission member (e.g., the transmission member 820) can have an outer diameter $d_o$ that is approximately 0.062 inches and an inner diameter $d_i$ that is approximately 0.042 inches. In this manner, the transmission member 820 can have a wall thickness of approximately 0.010 inches. In other embodiments, the outer diameter $d_o$ of the transmission member 820 can be between approximately 0.032 to 0.150 inches and the inner diameter $d_i$ can be between approximately 0.006 to 0.040 inches.

While various embodiments have been described above, it should be understood that they have been presented by way of example only, and not limitation. Where methods and/or schematics described above indicate certain events occurring in certain order, the ordering of certain events may be modified. Additionally certain events may be performed concurrently in parallel processes when possible, as well as performed sequentially. While the embodiments have been particularly shown and described, it will be understood that various changes in form and details may be made.

Although the transducer assembly 150 is shown in FIG. 2 as including two insulators 161 and two piezoelectric rings 162, in other embodiments, a transducer assembly can include any suitable number of insulators 161 and/or piezoelectric rings 162 in any suitable arrangement. Moreover, the insulators 161 can be formed from any suitable insulating material, ceramic materials (e.g., polyamide, expanded polytetrafluoroethylene (EPTFE), or the like). Similarly, the piezoelectric rings 162 can be any suitable piezoelectric material (e.g., lead zirkonate titanate (PZT-5), PZT-8, lead titanate (PT), lead metaniobate ($PbNbO_6$), polyvinylidene-fluoride (PVDF), or the like).

Although the assembly 700 is described above as applying ultrasonic energy to the transmission member 720, in other embodiments, ultrasonic energy can be supplied the sheath 790. In yet other embodiments, ultrasonic energy can be applied to both the sheath 1790 and the transmission member.

Although various embodiments have been described as having particular features and/or combinations of components, other embodiments are possible having a combination of any features and/or components from any of embodiments where appropriate. For example, any of the transmission members described herein can be included in the assembly 700 shown and described herein and/or can be used in conjunction with the sheath 790.

What is claimed is:

1. An apparatus, comprising:
a transmission member having a proximal end portion and a distal end portion, the transmission member configured to be inserted into a bodily lumen, the transmission member configured to transfer ultrasonic energy from the proximal end portion to the distal end portion, the transmission member defining a lumen along a longitudinal center line of the transmission member,
the distal end portion of the transmission member including a concave engagement surface and a distal end surface, the distal end surface defining a first opening in fluid communication with the lumen, the first opening intersects the longitudinal center line at an angle of between about 75 degrees and 105 degrees, the concave engagement surface configured to engage a target tissue within the bodily lumen to limit movement of the target tissue along the longitudinal center line, the concave engagement surface defining a second opening in fluid communication with the lumen; and
a sheath configured to be movably disposed about at least the distal end portion of the transmission member, the sheath including an engagement surface configured to engage the target tissue within the bodily lumen, the engagement surface of the sheath and the concave engagement surface of the transmission member configured to cooperatively limit movement of the target tissue along the longitudinal center line.

2. The apparatus of claim 1, wherein the concave engagement surface intersects the distal end surface.

3. The apparatus of claim 1, wherein the concave engagement surface is substantially continuous and is configured to surround at least a portion of the target tissue.

4. The apparatus of claim 1, wherein a length of the second opening along the longitudinal center line is less than about four times a diameter of the distal end portion of the transmission member.

5. The apparatus of claim 1, wherein the bodily lumen is a ureter and the target tissue is a calculus.

6. An apparatus, comprising:
a transmission member having a proximal end portion and a distal end portion, the transmission member configured to be inserted into a bodily lumen, the transmission member configured to transfer ultrasonic energy from the proximal end portion to the distal end portion, the transmission member defining a lumen along a longitudinal center line of the transmission member, the distal end portion of the transmission member including a first engagement surface and a distal end surface, the distal end surface defining a first opening in fluid communication with the lumen the first engagement surface defining a second opening in fluid communication with the lumen; and
a sheath configured to be movably disposed about at least the distal end portion of the transmission member, the sheath defining a second engagement surface, the first engagement surface and the second engagement surface configured to engage a target tissue within the bodily lumen to limit movement of the target tissue along the longitudinal center line.

7. The apparatus of claim 6, wherein the first engagement surface and the second engagement surface are collectively configured to surround at least a portion of the target tissue.

8. The apparatus of claim 6, wherein the first engagement surface is configured to engage a first side of the target tissue and the second engagement surface is configured to engage a second side of the target tissue, the second side opposite the first side.

9. The apparatus of claim 6, wherein the first engagement surface intersects the distal end surface, and the second engagement surface is disposed distally from the distal end surface of the transmission member.

10. The apparatus of claim 6, wherein:
the first engagement surface intersects the distal end surface of the transmission member; and
the sheath includes a distal end surface disposed distally from the distal end surface of the transmission member, the distal end surface of the sheath defining a plane that intersects the longitudinal center line at angle of between about 75 degrees and 105 degrees.

11. The apparatus of claim 6, wherein the bodily lumen is a ureter and the target tissue is a calculus.

12. The apparatus of claim 6, wherein the second engagement surface defines at least a portion of a sheath opening, the sheath opening configured to be aligned with the second opening of the transmission member.

13. A method, comprising:
inserting at least a distal end portion of an apparatus into a bodily lumen, the apparatus including a transmission member and a sheath, the transmission member defining a lumen along a longitudinal center line of the transmission member, the distal end portion of the transmission member including a first engagement surface, the first engagement surface defining an opening in fluid communication with the lumen, the sheath configured to be movably disposed about at least the distal end portion of the transmission member, the sheath defining a second engagement surface;
contacting a target tissue within the bodily lumen with the first engagement surface of the transmission member and the second engagement surface of the sheath to engage the target tissue, the first engagement surface exerting a lateral force against a first portion of the target tissue such that a second portion of the target tissue is maintained in contact with a wall defining the bodily lumen to limit movement of the target tissue along the longitudinal center line; and
transmitting ultrasonic energy from a proximal end portion of the transmission member towards the distal end portion such that a portion of the ultrasonic energy is delivered to the target tissue within the bodily lumen.

14. The method of claim 13, wherein:
the distal end portion of the transmission member includes a distal end surface, the distal end surface defining a plane that intersects the longitudinal center line at angle of between about 75 degrees and 105 degrees; and
at least one of the inserting or the contacting includes maintaining the distal end surface at a location outside of the target tissue.

15. The method of claim 13, wherein the bodily lumen is a ureter and the target tissue is a calculus.

16. The method of claim 13, wherein:
the contacting includes moving the sheath relative to the transmission member to engage the target tissue with the second engagement surface of the sheath.

17. The method of claim 13, further comprising:
aspirating at least a portion of the target tissue via the lumen defined by the transmission member.

* * * * *